(12) United States Patent
Cumba-Garcia et al.

(10) Patent No.: US 12,000,834 B2
(45) Date of Patent: Jun. 4, 2024

(54) METHODS AND MATERIALS FOR ASSESSING AND TREATING CANCER

(71) Applicant: Mayo Foundation for Medical Education and Research, Rochester, MN (US)

(72) Inventors: Luz M. Cumba-Garcia, Rochester, MN (US); Ian F. Parney, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 608 days.

(21) Appl. No.: 16/762,976

(22) PCT Filed: Nov. 9, 2018

(86) PCT No.: PCT/US2018/060040
§ 371 (c)(1),
(2) Date: May 11, 2020

(87) PCT Pub. No.: WO2019/094727
PCT Pub. Date: May 16, 2019

(65) Prior Publication Data
US 2020/0271656 A1    Aug. 27, 2020

Related U.S. Application Data

(60) Provisional application No. 62/584,291, filed on Nov. 10, 2017.

(51) Int. Cl.
| | |
|---|---|
| *G01N 33/53* | (2006.01) |
| *G01N 33/569* | (2006.01) |
| *G01N 33/574* | (2006.01) |
| *G01N 33/68* | (2006.01) |

(52) U.S. Cl.
CPC ....... *G01N 33/57488* (2013.01); *G01N 33/53* (2013.01); *G01N 33/56966* (2013.01); *G01N 33/574* (2013.01); *G01N 33/6863* (2013.01); *G01N 2333/5428* (2013.01); *G01N 2333/5437* (2013.01); *G01N 2333/57* (2013.01); *G01N 2333/70532* (2013.01); *G01N 2333/70596* (2013.01)

(58) Field of Classification Search
CPC ........... C12Q 2563/161; G01N 33/574; G01N 33/53; G01N 33/56966; G01N 2333/705; G01N 2333/70596; G01N 2333/71; G01N 2333/715; G01N 33/57488; G01N 33/6863; G01N 2333/57; G01N 2333/70532; G01N 2333/5428; G01N 2333/5437
See application file for complete search history.

(56) References Cited

U.S. PATENT DOCUMENTS

| | | |
|---|---|---|
| 2010/0151480 A1 | 6/2010 | Taylor et al. |
| 2010/0184046 A1 | 7/2010 | Klass et al. |
| 2020/0264185 A1* | 8/2020 | Xu ..................... G01N 33/6869 |

FOREIGN PATENT DOCUMENTS

| | | |
|---|---|---|
| WO | WO 2015130956 | 9/2015 |
| WO | WO-2016113361 A1 * | 7/2016 |

OTHER PUBLICATIONS

Chen et al. Protein content and functional characteristics of serum-purified exosomes from patients with colorectal cancer revealed by quantitative proteomics. Int J Cancer 140: 900-913, 2017 (online Nov. 3, 2016).*
Cumba-Garcia et al. Isolation and Analysis of Plasma-Derived Exosomes in Patients With Glioma. Front Oncol 9: 651, 2019.*
Li et al. Role of exosomal proteins in cancer diagnosis. Mol Cancer 16: 145, 2017.*
Reclusa et al. Exosomes as diagnostic and predictive biomarkers in lung cancer. J Thorac Dis 9(Suppl 13): S1373-S1382, 2017.*
Soung et al. Exosomes in cancer diagnosis. Cancers 9:8, Jan. 2017.*
Wang et al. Exosomes in tumor microenvironment: novel transporters and biomarkers. J Transl Med 14: 297, 2016.*
Witwer et al. Standardization of sample collection, isolation and analysis methods in extracellular vesicle research. J Extracellular Vesicles 2: 20360, 2013.*
Cumba Garcia et al., "Isolation and analysis of plasma-derived exosomes in patients with glioblastoma," Abstract, J. Immunology, May 1, 2018, 200(1S):178.37.
Cumba Garcia et al., "Optimized isolation of plasma extracellular vesicles for use as potential biomarkers in patients with glioblastoma," Poster, Presented at Proceedings of the Society for Neuroscience Meeting, Washington, DC, Nov. 11, 2017, 1 page.
Das et al., "Angiogenesis in Glioblastoma," N. Engl. J. Medicine, Oct. 17, 2013, 369(16):1561-1563.
Dea et al., "Does extent of resection impact survival in patients bearing glioblastoma?," Can. J. Neural. Sciences, Sep. 2012, 39(5):632-637.
Figueroa et al., "Detection of wild-type EGFR amplification and EGFRvIII mutation in CSF-derived extracellular vesicles of glioblastoma patients," Neuro-Oncology, Apr. 27, 2017, 19(11):1494-1502.
Gustafson et al., "Systemic immune suppression in glioblastoma: the interplay between CD141HLA-DRlo/neg monocytes, tumor factors, and dexamethasone," Neuro-Oncology, Feb. 23, 2010, 12(7):631-644.
Haderk et al., "Tumor-derived exosomes modulate PD-L1 expression in monocytes," Sci. Immunology, Jul. 28, 2017, 2(13):eaah5509, 12 pages.
Koch et al., "Microvesicles as a Biomarker for Tumor Progression versus Treatment Effect in Radiation/Temozolomide-Treated Glioblastoma Patients," Transl. Oncology, Dec. 2014, 7(6):752-758.

(Continued)

*Primary Examiner* — Bridget E Bunner
(74) *Attorney, Agent, or Firm* — Fish & Richardson P.C.

(57) ABSTRACT

This document relates to methods and materials for identifying and/or treating mammals having cancer. For example, small extracellular vesicles (EVs), such as exosomes, obtained from a mammal suspected of having a cancer can be used to identify the mammal as having cancer and, optionally, the mammal can be treated.

9 Claims, 23 Drawing Sheets

(56) References Cited

OTHER PUBLICATIONS

Kruser et al., "Pseudoprogression after glioma therapy: a comprehensive review," Expert Rev. Neurotherapy, Apr. 2, 2013, 13(4):389-403.

Lacroix et al., "A multivariate analysis of 416 patients with glioblastoma multiforme: prognosis, extent of resection, and survival," J. Neurosurgery, Aug. 2001, 95(2):190-198.

Mahmoudi et al., "Small extracellular vesicles as tumor biomarkers for glioblastoma," Mol. Aspects Medicine, Nov. 2015, 45:97-102.

Nakamura et al., "Genetic analysis to complement histopathological diagnosis of brain tumors," Histol. Histopathology, Mar. 2007, 22(3):327-335.

PCT International Preliminary Report on Patentability in International Appln. No. PCT/US2018/060040, dated May 12, 2020, 7 pages.

PCT International Search Report and Written Opinion in International Appln. No. PCT/US2018/060040, dated Jan. 16, 2019, 9 pages.

Ricklefs et al., "Immune evasion mediated by PD-LI on glioblastoma-derived extracellular vesicles," Sci. Advances, Mar. 7, 2018, 4(3):eaar2766, 15 pages.

Rodrigues et al., "Normal human monocytes exposed to glioma cells acquire myeloid-derived suppressor cell-like properties," Neuro-Oncology, Dec. 22, 2009, 12(4):351-365.

Stupp et al., "Radiotherapy plus Concomitant and Adjuvant Temozolomide for Glioblastoma," N. Engl. J. Medicine, Mar. 10, 2005, 352(10):987-996.

Takei et al., "New Immunohistochemical Markers in the Evaluation of Central Nervous System Tumors: A Review of 7 Selected Adult and Pediatric Brain Tumors," Arch. Pathol. Lab Medicine, Feb. 2007, 131(2):234-241.

Treps et al., "Glioblastoma stem-like cells secrete the pro-angiogenic VEGF-A factor in extracellular vesicles," J. Extracell. Vesicles, Aug. 2017, 8(1):1359479, 12 pages.

EFSA Scientific Committee, "Statistical Significance and Biological Relevance," EFSA Journal, Sep. 2011, 9(9):2372, 17 pages.

\* cited by examiner

Grades 2, 3 and 4

IDH WT and Mutant

METHODS AND MATERIALS FOR ASSESSING AND TREATING CANCER

CROSS-REFERENCE TO RELATED APPLICATIONS

This application is a National Stage application under 35 U.S.C. § 371 of International Application No. PCT/US2018/060040, having an International Filing Date of Nov. 9, 2018, which claims the benefit of U.S. Patent Application Ser. No. 62/584,291, filed on Nov. 10, 2017. The disclosure of the prior application is considered part of (and is incorporated by reference in) the disclosure of this application.

BACKGROUND

1. Technical Field

This document relates to methods and materials involved in identifying and/or treating mammals having cancer. For example, small extracellular vesicles (EVs), such as exosomes, obtained from a mammal suspected of having a cancer can be used to identify the mammal as having cancer and, optionally, the mammal can be treated.

2. Background Information

Gliomas, including glioblastoma (GBM), are the most common malignant brain tumors with more than 18,000 newly diagnosed patients every year in the United States and are highly lethal (Stupp et al., 2005 *N Engl J Med.* 352:987-996). Despite aggressive treatment with surgery, radiation, and chemotherapy, GBM remains nearly universally fatal within five years. Initial diagnosis of GBM typically relies on magnetic resonance imaging (MRI), but tissue histopathology with associated prognostic evaluations using immunohistochemistry or genetic techniques (Takei et al., 2007 *Arch Pathol Lab Med.* 131:234-241; and Nakamura et al., 2007 *Histol Histopathol.* 22:327-335) is required for definitive diagnosis. Post-operative imaging is performed to evaluate the extent of surgical resection and evaluate tumor progression. However, MRI inadequately correlates with actual neoplastic disease burden, failing to address the micro-infiltrative disease beyond the borders of radiological depiction (Das et al., 2013 *N Engl J Med.* 369:1561-1563; Dea et al., 2012 *Can J Neurol Sci.* 39:632-637; and Lacroix et al., 2001 *J Neurosurg.* 95:190-198). Furthermore, MRI can be difficult to interpret after treatment due to inflammation and necrosis in response to radiation, chemotherapy or immunotherapy. False positives of MRI imaging due to treatment-related inflammation called "pseudo-progression" occur frequently (Koch et al., 2014 *Transl Oncol.* 7:752-758; and Kruser et al., 2013 *Expert Rev Neurother.* 13:389-403) and clinicians are faced with the challenge of determining if the image reflects treatment-related effects or true tumor progression (Mahmoudi et al., 2015 *Mol Aspects Med.* 45:97-102). Given this limitation, there is a definitive need for improved, non-invasive methods of diagnosing GBM and monitoring these tumors throughout treatment.

SUMMARY

This document provides methods and materials involved in identifying and/or treating mammals having cancer. For example, small EVs, such as exosomes, obtained from a mammal suspected of having a cancer can be used to identify the mammal as having cancer and, optionally, the mammal can be treated. In some cases, a sample obtained from a mammal having, or suspected of having, a cancer can be assessed for the presence, absence, or level of one or more cargoes in one or more EVs, and the mammal can be identified as having cancer based, at least in part, on the presence, absence, or level of one or more cargoes in the EVs. In some cases, a mammal identified as having cancer based, at least in part, on the presence, absence, or level of one or more cargoes in the EVs isolate from a sample obtained from the mammal can be treated by administering one or more cancer treatments to the mammal.

As demonstrated herein, density gradient ultracentrifugation (DGU) can be used to isolate a pure exosome population from normal donors' and GBM patients' plasma. Also as demonstrated herein, plasma exosomes from GBM patients have distinct cargo from healthy donors. For example, GBM patient exosomes had tumor-specific cargo such as tumor antigens (e.g., a tumor-specific mutant isocitrate dehydrogenase 1 (IDH1)) and had reduced immunomodulatory molecules (e.g., IFN-γ, IL-10, IL-13, B7-1, B7-2, and ICOSL). Glioma EVs, especially exosomes, in plasma have biological effects such as mediating immunosuppression and contain signature tumor-specific cargo, therefore could serve as liquid biopsies.

The ability to use a simple, non-invasive technique based on plasma exosomes provides a unique and unrealized opportunity for early detection of GBM, early treatment of GBM, and/or the ability to monitor GBM treatment response, post-surgery response, and post-surgery recurrence. As such, the methods described herein can use liquid biopsies not only for early cancer detection allowing for early treatment, but can also be used to identify a patient as not having cancer (e.g., after receiving a false positive by another method such as MRI imaging) and can spare the patient from undergoing unnecessary treatment.

In general, one aspect of this document features methods for treating mammals having cancer. The methods can include, or consist essentially of, identifying EVs in a sample from a mammal, where the EVs have reduced levels of one or more immunomodulatory polypeptides, and administering a cancer treatment to the mammal. The mammal can be a human. The cancer can be a glioblastoma, breast cancer, prostate cancer, ovarian cancer, bladder cancer, head and neck cancer, melanoma, lung cancer, renal cell carcinoma, colon cancer, pancreatic cancer, leukemia, lymphoma, thyroid cancer, or osteosarcoma. The cancer can be a glioblastoma. The sample can be a blood sample (e.g., plasma). The EVs can be exosomes. The longest diameter of the exosomes can be less than about 100 nm. The longest diameter of the exosomes can be from about 50 nm to about 100 nm. The one or more immunomodulatory polypeptides can include a cytokine (e.g., IFN-γ, IL-10, IL-13, IL-2, IL-4, IL-5, IL-6, IL-8, GM-CSF, and TNF-α). The one or more immunomodulatory polypeptides can include an immune checkpoint polypeptide (e.g., CD80, CD86, PD-L1, ICOSL, CD276, CD28, CTLA-4, CD278, PD-1, and PD-L2). The one or more immunomodulatory polypeptides can include IFN-γ, IL-10, IL-13, CD80, CD86, and ICOSL. The cancer treatment can include surgery, radiation therapy, chemotherapy, tumor treating fields (TTF) therapy, targeted therapy, hormone therapy, angiogenesis inhibitor therapy, tumor vaccination, checkpoint blockade therapy, and any combinations thereof.

In another aspect, this document features methods for treating mammals having cancer. The methods can include, or consist essentially of, administering a cancer treatment to a mammal identified as having EVs in a sample from the mammal, where the EVs have reduced levels of one or more immunomodulatory polypeptides. The mammal can be a human. The cancer can be a glioblastoma, breast cancer, prostate cancer, ovarian cancer, bladder cancer, head and neck cancer, melanoma, lung cancer, renal cell carcinoma, colon cancer, pancreatic cancer, leukemia, lymphoma, thyroid cancer, or osteosarcoma. The cancer can be a glioblastoma. The sample can be a blood sample (e.g., plasma). The EVs can be exosomes. The longest diameter of the exosomes can be less than about 100 nm. The longest diameter of the exosomes can be from about 50 nm to about 100 nm. The one or more immunomodulatory polypeptides can include a cytokine (e.g., IFN-γ, IL-10, IL-13, IL-2, IL-4, IL-5, IL-6, IL-8, GM-CSF, and TNF-α). The one or more immunomodulatory polypeptides can include an immune checkpoint polypeptide (e.g., CD80, CD86, PD-L1, ICOSL, CD276, CD28, CTLA-4, CD278, PD-1, and PD-L2). The one or more immunomodulatory polypeptides can include IFN-γ, IL-10, IL-13, CD80, CD86, and ICOSL. The cancer treatment can include surgery, radiation therapy, chemotherapy, TTF therapy, targeted therapy, hormone therapy, angiogenesis inhibitor therapy, tumor vaccination, checkpoint blockade therapy, and any combinations thereof.

In another aspect, this document features methods for detecting one or more immunomodulatory polypeptides in a sample (e.g., a sample obtained from a mammal). The methods can include, or consist essentially of, isolating a substantially pure population of exosomes from a sample obtained from a mammal, where the isolating consists of an ultracentrifugation step at from about 70,000×g to about 200,000×g for from about 60 minutes to about 24 hours; and detecting the level of the immunomodulatory polypeptides in the exosomes. The mammal can be a human. The sample can be a blood sample (e.g., plasma). The isolating can consist of an ultracentrifugation step at about 102,000×g for about 90 minutes.

In another aspect, this document features methods for identifying mammals as having a cancer. The methods can include, or consist essentially of, isolating a substantially pure population of exosomes from a sample obtained from a mammal, where the isolating consisting of an ultracentrifugation step at from about 70,000×g to about 200,000×g for from about 60 minutes to about 24 hours; detecting the level of one or more immunomodulatory polypeptides in the exosomes; and identifying the mammal as having cancer when a reduced level of the immunomodulatory polypeptides are detected in the exosomes. The mammal can be a human. The cancer can be a glioblastoma, breast cancer, prostate cancer, ovarian cancer, bladder cancer, head and neck cancer, melanoma, lung cancer, renal cell carcinoma, colon cancer, pancreatic cancer, leukemia, lymphoma, thyroid cancer, and osteosarcoma. The cancer can be a glioblastoma. The sample can be a blood sample (e.g., plasma). The isolating can consist of an ultracentrifugation step at about 102,000×g for about 90 minutes.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
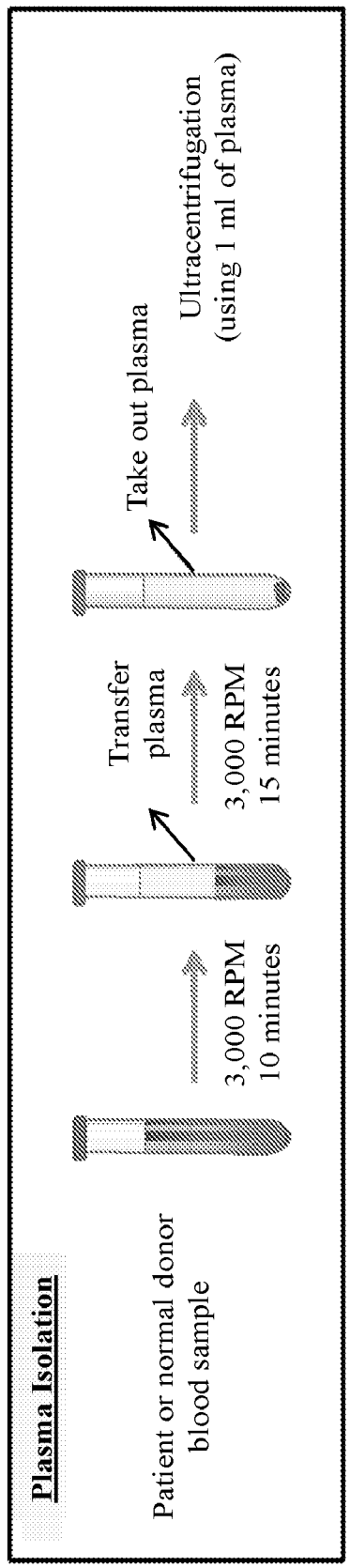
FIGS. 1A and 1B contain schematics showing plasma exosome isolation by density gradient ultracentrifugation. (A) Whole blood samples collected in EDTA tubes underwent brief centrifugation (3000 RPM×10 minutes) for plasma isolation. The isolated plasma was transferred to a fresh tube and spun for 15 minutes at 3000 RPM to remove any remaining cellular debris and erythrocytes. (B) Density gradient ultracentrifugation to purify exosomes was performed by mixing 1 ml of plasma with 1 ml of 50% OptiPrep solution. Eleven ml of 10% OptiPrep was layered on top of the homogenized solution and this underwent ultracentrifugation for 90 minutes at 24,000 RPM (Spin 1). The top layer (10 ml) was collected. A portion was used for nanotracker particle analysis and nanoscale flow cytometry analysis while the remainder underwent ultracentrifugation at 24,000 RPM for 16 hours (Spin 2). The supernatant was discarded and the pellet was resuspended in a total volume of 200 μl. Further analysis (nanoparticle tracking, western blots, protein arrays, and enzyme-linked immunosorbent assays (ELISAs)) was performed using this final, concentrated solution.

This document provides methods and materials for identifying and/or treating mammals having cancer. For example, EVs, such as exosomes, obtained from a mammal suspected of having a cancer can be used to identify the mammal as having cancer and, optionally, the mammal can be treated. In some cases, a sample obtained from a mammal having, or suspected of having, a cancer can be assessed for the presence, absence, or level of one or more cargoes in one or more EVs, and the mammal can be identified as having cancer based, at least in part, on the presence, absence, or level of one or more cargoes in the EVs. In some cases, a mammal identified as having cancer based, at least in part, on the presence, absence, or level of one or more cargoes in the EVs isolate from a sample obtained from the mammal can be treated by administering one or more cancer treatments to the mammal.

EVs, including exosomes, are small particles released from cancer cells into the tumor microenvironment and the bloodstream. EVs are self-contained within their own plasma membrane and contain cargo reflecting their cell of origin. In some cases, when a cancer includes cancer cells expressing a particular antigen, the EVs (e.g., exosomes) released from cancer cells into the tumor microenvironment and the bloodstream also can carry that antigen as cargo and, optionally, can present that antigen on their surface. In some cases, EVs (e.g., exosomes) released from cancer cells into the tumor microenvironment and the bloodstream can be used to identify a tumor antigen expressed by cancer cells within a mammal. For example, EVs (e.g., exosomes) released from cancer cells into the tumor microenvironment and the bloodstream can include tumor-specific signatures.

An EV can be any appropriate EV (e.g., an exosome, a microvesicle (MV), or an apoptotic body). In some cases, an EV can be an exosome. As used herein, an exosome can be any EV having a size (e.g., a longest diameter) of a less than about 100 nm (e.g., about 90 nm, about 80 nm, about 75 nm, about 70 nm, about 65 nm, about 60 nm, about 55 nm, or about 50 nm in size). For example, an exosome can be from about 50 nm to about 100 nm (e.g., from about 50 nm to about 90 nm, from about 50 nm to about 80 nm, from about 50 nm to about 70 nm, from about 50 nm to about 60 nm, from about 60 nm to about 100 nm, from about 70 nm to about 100 nm, from about 80 nm to about 100 nm, from about 90 nm to about 100 nm, from about 60 nm to about 90 nm, from about 70 nm to about 80 nm, from about 60 nm to about 80 nm, or from about 70 nm to about 90 nm) in size. In some cases, an EV can include (e.g., can express) one or more CD63 polypeptides. In some cases, an EV can include (e.g., can express) one or more flotillin-1 polypeptides. In some cases, an EV can include (e.g., can express) one or more programmed death-ligand 1 (PD-L1) polypeptides.

Any appropriate mammal having, or suspected of having, a cancer can be identified and/or treated as described herein. Examples of mammals having, or suspected of having, a cancer can be identified and/or treated as described herein include, without limitation, humans, non-human primates (e.g., monkeys), dogs, cats, horses, cows, pigs, sheep, goat, mice, and rats. For example, a human having, or suspected of having, a cancer can be identified and/or treated as described herein.

When treating a mammal (e.g., a human) having, or suspected of having, a cancer as described herein, the cancer can be any type of cancer. In some cases, a cancer can be a blood cancer. In some cases, a cancer can include one or more solid tumors. In some cases, a cancer can be a recurrent cancer. In some cases, a cancer can be a primary cancer. In some cases, a cancer can be a metastatic cancer. In some cases, a cancer can be a chemo-resistant cancer. Examples of cancers that can be identified and/or treated by as described herein include, without limitation, brain cancers (e.g., GBMs), breast cancers, prostate cancers, ovarian cancers, bladder cancers, head and neck cancers, skin cancers (e.g., melanoma), lung cancers, renal cell carcinomas, gastrointestinal cancers (e.g., colon cancer and pancreatic cancer), hematological cancers (e.g. leukemia and lymphoma), endocrine cancers (e.g., thyroid cancer), and bone cancers (e.g., osteosarcoma). In some cases, a human having a GBM can be identified and/or treated as described herein.

In some cases, methods described herein can include identifying a mammal (e.g., a human) as having a cancer. Any appropriate method can be used to identify a mammal as having a cancer. For example, imaging techniques and/or biopsy techniques can be used to identify mammals (e.g., humans) having cancer.

In some cases, assessing one or more EVs (e.g., one or more exosomes) in a sample from a mammal for the presence, absence, or level of one or more cargoes can be used for identifying a mammal as having a cancer. For example, a sample obtained from a mammal having, or suspected of having, a cancer can be assessed for the presence, absence, or level of one or more cargoes in one or more EVs. In some cases, the methods provided herein can include isolating one or more EVs (e.g., one or more exosomes) from a sample obtained from a mammal (e.g., a mammal having, or suspected of having, a cancer). Any appropriate method can be used to isolate one or more EVs from a sample. In some cases, EVs isolated from a sample are single EVs (e.g., are not present in any aggregate). For example, ultrafiltration, size exclusion chromatography (SEC), flow field-flow fractionation (F4), sequential filtration, differential ultracentrifugation (e.g., including a plurality of centrifugation steps such as a low-speed centrifugation step and a high-speed ultracentrifugation step), and DGU (e.g., DGU using sucrose gradient fractions) can be used to isolate one or more EVs from a sample. In some cases, a method for isolating one or more EVs from include a single step. For example, exosomes can be isolated from plasma from a mammal using a single ultracentrifugation step at a relative centrifugal force (RCF) of from about 70,000×g to about 200,000×g (e.g., from about 70,000×g to about 175,000×g, from about 70,000×g to about 150,000×g, from about 70,000×g to about 125,000×g, from about 70,000×g to about 100,000×g, from about 75,000×g to about 200,000×g, from about 100,000×g to about 200,000×g, from about 125,000×g to about 200,000×g from about 150,000×g to about 200,000×g from about 175,000×g to about 200,000×g from about 75,000×g to about 175,000×g from about 100,000×g to about 150,000×g from about 75,000×g to about 100,000×g, from about 100,000×g to about 125,000×g, from about 125,000×g to about 150,000×g, or from about 150,000×g to about 175,000×g). In some cases, exosomes can be isolated from plasma from a mammal using a single ultracentrifugation step at a RCF of about 73,000×g. In some cases, exosomes can be isolated from plasma from a mammal using a single ultracentrifugation step at a RCF of about 102,000×g. For example, exosomes can be isolated from plasma from a mammal using a single ultracentrifugation step that lasts for from about 1 hour (e.g., 60 minutes) to about 24 hours (e.g., from about 1 hour to about 20 hours, from about 1 hour to about 18 hours, from about 1 hour to about 15 hours, from about 1 hour to about 12 hours, from about 1 hour to about 10 hours, from about 1 hour to about 7 hours, from about 1 hour to about 5 hours, from about 1 hour to about 3 hours, from about 2 hours to about 24 hours, from about 5 hours to about 24 hours, from about 8 hours to about 24 hours, from about 10 hours to about 24 hours, from about 12 hours to about 24 hours, from about 15 hours to about 24 hours, from about 17 hours to about 24 hours, from about 20 hours to about 24 hours, from about 2 hours to about 20 hours, from about 6 hours to about 12 hours, from about 2 hours to about 4 hours, from about 4 hours to about 6 hours, from about 6 hours to about 12 hours, or from about 12 hours to about 20 hours) In some cases, exosomes can be isolated from plasma from a mammal using a single ultracentrifugation step that lasts about 1.5 hours (e.g., about 90 minutes). In some cases, the isolation of one or more EVs from a sample can be confirmed using any appropriate method (e.g., nanoscale flow cytometry and/or nanoparticle tracking analyzer instruments). In some cases, EVs isolated as described herein can include a pure or a substantially pure population of EVs. For example, a pure or a substantially pure population of exosomes can include greater than about 95% exosomes (e.g., about 95% exosomes, about 96% exosomes, about 97% exosomes, about 98% exosomes, about 99% exosomes, or about 100% exosomes).

One or more EVs (e.g., one or more exosomes) can be isolated from any appropriate sample (e.g., a sample from a mammal having, or suspected of having, a cancer). In some cases, a sample can be a liquid sample (e.g., a liquid biopsy). Examples of samples from which EVs can be isolated include, without limitation, blood samples (e.g., whole blood, plasma, and serum), aqueous humor samples, amniotic fluid samples, saliva samples, cerebral spinal fluid samples, synovial fluid samples, tissues samples (e.g., adipose tissue samples), urine samples, and seminal fluid samples. For example, one or more EVs (e.g., one or more exosomes) can be isolated from a plasma sample obtained from a mammal having, or suspected of having, a cancer.

In some cases, the presence, absence, or level of one or more cargoes in one or more EVs (e.g., one or more exosomes) isolated from a sample obtained from a mammal can be used to identify the mammal as having cancer. An EV (e.g., an exosome) can include any appropriate cargo. In some cases, an EV can encapsulate a cargo. In some cases, an EV can present a cargo (e.g., can present a cargo on its surface). Examples of cargoes that can be included in an EV include, without limitation, one or more immunomodulatory polypeptides (e.g., one or more pro-inflammatory cytokines and/or one or more immune checkpoint polypeptides), one or more tumor antigens, one or more angiogenic proteins, one or more microRNAs, one or more mRNAs, one or more short non-coding nucleotides (e.g., one or more non-coding RNAs and/or one or more non-coding DNAs), and one or more heat shock proteins.

In some cases, one or more EVs (e.g., one or more exosomes) present in a mammal having, or suspected of having, a cancer can include reduced levels of one or more immunomodulatory polypeptides. In some cases, an immunomodulatory polypeptide can be an immunosuppressive polypeptide. In some cases, an immunomodulatory polypeptide can be a cytokine. In some cases, an immunomodulatory polypeptide can be a pro-inflammatory polypeptide. In some cases, an immunomodulatory polypeptide can be an immune checkpoint polypeptide (e.g., co-inhibitory molecules and co-stimulatory molecules). Examples of immunomodulatory polypeptides that can be present in reduced levels an EV present in a mammal having, or suspected of having, a cancer, can include, without limitation IFN-γ, IL-10, IL-13, IL-2, IL-4, IL-5, IL-6, IL-8, GM-CSF, TNF-α, CD80, CD86, PD-L1, ICOSL, CD276, Tp44, CTLA-4 (CD152), ICOS (CD278), PD-1 (CD279), and PD-L2 (B7-DC). For example, an EV present in a mammal having, or suspected of having, a cancer, can include reduced levels of IFN-γ, IL-10, and/or IL-13. For example, an EV present in a mammal having, or suspected of having, a cancer, can include reduced levels of B7-1 (CD80), B7-2 (CD86), and/or B7-H2 (ICOS L). For example, an EV present in a mammal having, or suspected of having, a cancer, can include reduced levels of IFN-γ, IL-10, IL-13, B7-1 (CD80), B7-2 (CD86), and B7-H2 (ICOS L). In some cases, immunomodulatory polypeptides that can be present in reduced levels in an EV present in a mammal having, or suspected of having, a cancer can be as described in Table 1. In some cases, cell cycle checkpoint polypeptides that can be present in reduced levels in an EV present in a mammal having, or suspected of having, a cancer can be as described in Table 2. In some cases, immunomodulatory polypeptides that can be present in reduced levels in an EV present in a mammal having, or suspected of having, a cancer, can be as described elsewhere (see, e.g., Rodrigues et al., 2010, *Neuro Oncol.* 12:351-65; Gustafson et al., 2010, *Neuro Oncol.* 12:631-44; and Ricklefs et al., 2018, *Sci Adv,* 4:eaar2766).

The term "reduced level" as used herein, for example, with respect to a level of one or more immunomodulatory polypeptides refers to any level that is less than a reference level of one or more immunomodulatory polypeptides. The term "reference level" as used herein, for example, with respect to one or more immunomodulatory polypeptides refers to the level of one or more immunomodulatory polypeptides typically observed in a sample (e.g., a control sample) from one or more mammals (e.g., humans) without cancer. Control samples can include, without limitation, samples from normal (e.g., healthy) mammals, and cell lines (e.g., non-tumor forming cells lines). In some cases, a reduced level of one or more immunomodulatory polypeptides can be a level that is about least 2 (e.g., at least 3, at least 4, at least 5, at least 6, at least 7, at least 8, at least 9, or at least 10) fold less than a reference level of one or more immunomodulatory polypeptides. It will be appreciated that levels from comparable samples are used when determining whether or not a particular level is a reduced level.

In some cases, one or more EVs (e.g., one or more exosomes) present in a mammal having, or suspected of having, a cancer can include one or more tumor antigens. Examples of tumor antigens that can be present in an EV present in a mammal having, or suspected of having, a cancer, can include, without limitation, human epidermal growth factor receptor 2 (HER2), epidermal growth factor receptors (EGFRs; e.g., modified EGFRvIIIs), CD19, CD20, CD47, epithelial cell adhesion molecule (EpCAM), CD33, CD123, CLL1, CD5, CD7, CD2, CD22, c-MET, TROP2, CEA, E-Cadherin, c-kit, ROR1, B-cell maturation antigen (BCMA), mucin 1 (MUC-1), estrogen receptor (ER), epidermal growth factor receptor (EGFR), folate receptor alpha, mesothelin, alphafetoprotein (AFP), carcinoembryonic antigen (CEA), CA-125, epithelial tumor antigen (ETA), and melanoma-associated antigen (MAGE), and tumor-specific modifications (e.g., mutations) of polypeptides such as a tumor-specific isocitrate dehydrogenase 1 (IDH1) polypeptides. In some cases, tumor antigens that can be present in an EV present in a mammal having, or suspected of having, a cancer, can be as described elsewhere (see, e.g., Figueroa et al., 2017, *Neuro Oncol* 19:1494-1502).

In some cases, one or more EVs (e.g., one or more exosomes) present in a mammal having, or suspected of having, a cancer can include one or more angiogenic proteins. Examples of angiogenic proteins that can be present in an EV present in a mammal having, or suspected of having, a cancer, can include, without limitation, fibroblast growth factors (FGFs), vascular endothelial growth factors (VEGFs), angiopoietins, and matrix metalloproteinases (MMPs). In some cases, angiogenic proteins that can be present in an EV present in a mammal having, or suspected of having, a cancer, can be as described elsewhere (see, e.g., Treps et al., 2017, *J Extracell Vesicles* 8: 1359479).

Any appropriate method can be used to determine the presence, absence, or level of a cargo in an EV. For example, cytometry methods (e.g., flow cytometry such as cell sorting), spectrometry methods, ELISAs, immunoprecipitation, immunoelectrophoresis, western blotting, protein immunostaining, RNA-arrays, RNA sequencing, proteomics, and/or metabolomics can be used to determine the presence, absence, or level of a cargo in an EV.

Once identified as having a cancer based, at least in part, on the presence, absence, or level of one or more cargoes in EVs isolate from a sample obtained from the mammal can be treated by administering one or more cancer treatments to the mammal. For example, a mammal (e.g., a human) identified as having a cancer can be administered, or instructed to self-administer, one or more cancer treatments. Examples of cancer treatments include, without limitation, surgery (e.g., to remove the tumor), radiation therapies, chemotherapies (e.g., temozolomide), tumor treating fields (TTF) therapies, targeted therapies (e.g., monoclonal antibody therapies such as bevacizumab), hormonal therapies, angiogenesis inhibitors, tumor vaccinations, checkpoint blockade therapies, cancer immunotherapies, and any combinations thereof. In cases where one or more EVs (e.g., one or more exosomes) present in a mammal having, or suspected of having, a cancer include one or more tumor antigens, the tumor antigens can be used to select a treatment for a mammal from which the EVs were obtained. For example, a mammal having EVs including a particular tumor antigen can be treated by administering a cancer treatment to the mammal that targets that particular tumor antigen.

In some cases, treating a mammal having a cancer as described herein can be effective to reduce the severity of the cancer.

In some cases, treating a mammal having a cancer as described herein can be effective to reduce one or more symptoms of the cancer in the mammal. For example, the treatment can reduce the number of cancer cells within a mammal. For example, the treatment can reduce the size (e.g., volume) of one or more tumors within a mammal.

The invention will be further described in the following examples, which do not limit the scope of the invention described in the claims.

EXAMPLES

Example 1

Isolation and Analysis of Plasma-Derived Exosomes in Patients with Glioblastoma

This example evaluates a simple, effective two-step technique for exosome purification from GBM patients and normal donors' plasma. Analysis of these exosomes showed clearly measurable differences between brain cancer patients and normal donors, indicating the potential utility of this technique to develop liquid biopsies to accurately to diagnose and monitor glioblastomas without brain biopsies.

Materials and Methods

Patients

This was a Mayo Clinic Institutional Review Board (Mayo Clinic IRB#15-006351) approved and Health Insurance Portability and Accountability Act (HIPAA) compliant study. Written informed consent was obtained from all subjects. In the following sections, we first describe our patient cohort and the methods used to isolate and characterize plasma exosomes and subsequently we describe the techniques used to analyze the immunosuppressive role of these particles.

Blood Collection and Plasma Isolation

We prospectively included blood samples from 40 subjects, consisting of 19 anonymized control samples from normal donors obtained through Mayo Clinic (Rochester) blood bank and 19 samples from glioma patients undergoing surgery. From this 19 glioma patients, 6 were females between the ages of 35-67 and 13 were male between the ages of 27-73. All samples were acquired through collection of normal, whole blood in ethylenediaminetetraacetic acid (EDTA) tubes. After blood collection, the samples were spun at 3,000 RPM (Eppendorf Centrifuge 5810 No. 0012529-rotor A-4-81) for 10 minutes. Plasma isolated from blood was then transferred into a 15 ml conical tube (Falcon No. 352097) and spun at 3,000 RPM for 15 minutes (FIG. 1A). One to nine ml of plasma were recovered from each sample and stored in a sterile cryogenic vial (Corning Incorporated No. 430488) at −20° C.

Isolation of Exosomes

Figure 1B:
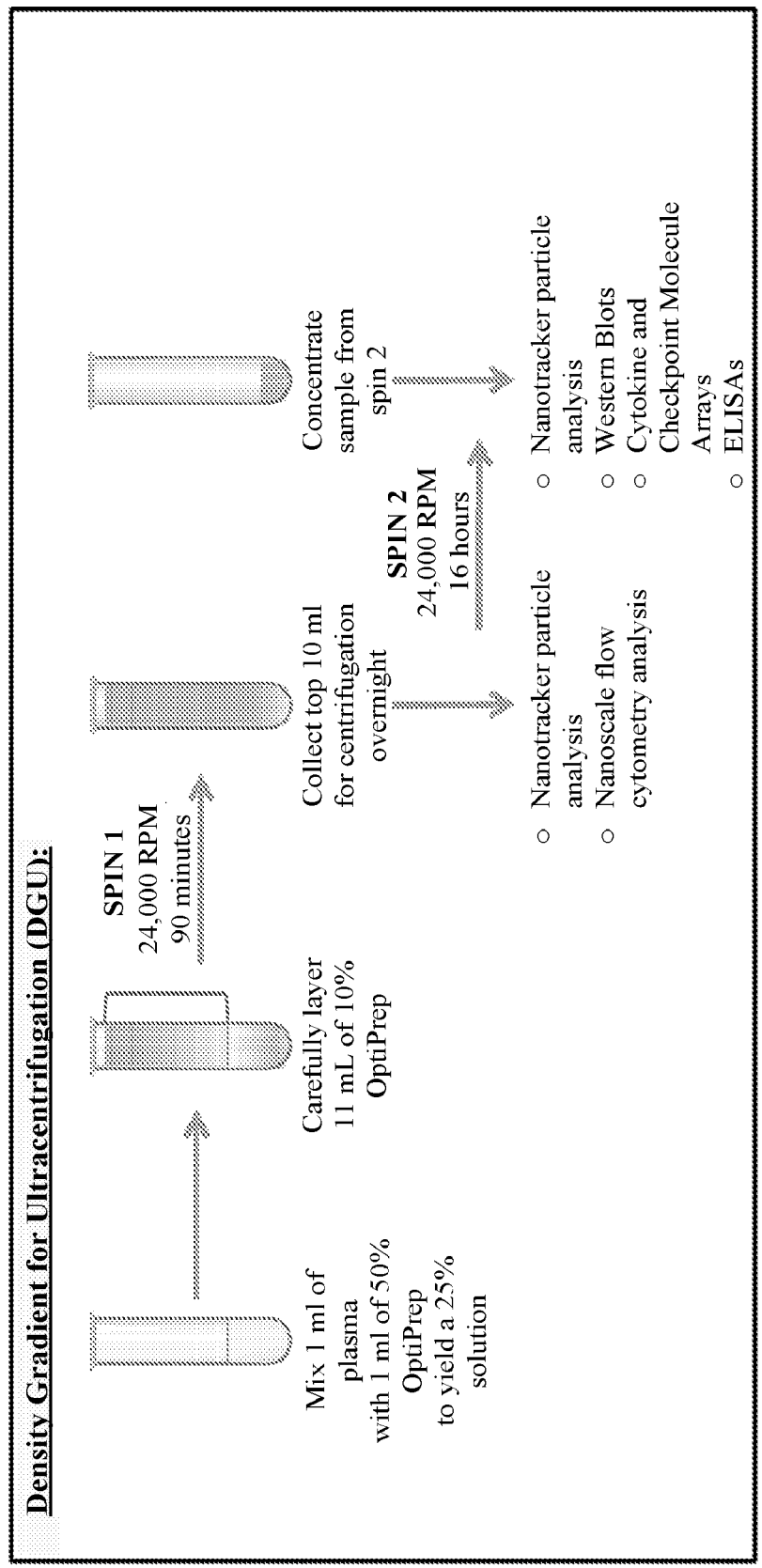

Exosomes from plasma were isolated by ultracentrifugation using a density gradient (FIG. 1B). One ml of the previously stored and frozen plasma was thawed and mixed in an ultra-clear centrifuge tube (Beckman Coulter No. 344060) with 1 ml of a 50% OptiPrep solution (45 ml of OptiPrep Density Gradient Medium, Sigma-Aldrich No. D1556, and 9 ml of OptiPrep diluent) (OptiPrep diluent preparation: 5 ml of 2.5 M sucrose, 0.1 g (6 mM) of EDTA, 1.08 g (120 mM) of Tricine at pH 7.8 and 45 ml of water). Next, 11 ml of a 10% OptiPrep solution (4.4 ml of 50% OptiPrep solution and 17.6 ml of buffer A: 100 mL of 2.5 M sucrose, 0.34 g (1 mM) of EDTA, 3.58 g (20 mM) of Tricine at pH 7.8 and 900 ml of water) were carefully layered onto the homogenized solution inside the tube. Samples were spun at 24,000 RPM (Beckman Coulter Optima LE-80K Ultracentrifuge-rotor SW40 Ti No. 99U 10480) for 90 minutes. Nanotracker particle analysis using NanoSight (Malvern, NanoSight NS300) was performed using 10 µl from the bottom of the solution diluted into 990 µl of PBS (1:100). The top 10 ml of the solution were transferred to a new ultracentrifuge tube, and 1 ml was taken for nanoscale flow cytometry analysis. Samples were spun at 24,000 RPM for 16 hours afterward. Samples from the second spin were then concentrated in 200 µl, by aspirating part of the solution, for western blots, cytokine and checkpoint molecules arrays, and ELISA assays. Nanotracker particle analysis was performed again to compare the particles obtained in both spins.

Nanoscale Flow Cytometry

The A50-Micro Nanoscale Flow Cytometer (Apogee Flow Systems Inc. No. S/N0105) was utilized to compare the total microparticles from GBM patients' and normal donors' unsorted whole plasma to exosomes samples isolated employing our DGU one-step protocol (exosome samples collected from spin 1-90 minutes). Whole plasma or exosomes isolated by DGU were diluted 1:40 in PBS to quantify microvesicle and exosome populations in each sample. Exosomes were defined as events less than 100 nm in size. Particles sizes were determined by using Apogee calibration bead mix (Catalog No. 1493) composed of 180, 240, 300, 590, 880, and 1300 nm beads, and Apogee flow cytometer calibration beads (Catalog No. 1517) composed of 80 and 100 nm beads. The samples were measured in triplicates.

Cytokine and Checkpoint Molecules Arrays

Arrays to evaluate Th1 and Th2 cytokines (Quantibody Human TH1/TH2 Array 1, RayBiotech No. QAH-TH-1) and checkpoint molecules (Quantibody Human Immune Checkpoint Molecule Array 1, RayBiotech No. QAH-ICM-1) present in isolated plasma exosomes from 4 GBM patients and 4 normal donors were carried out per the manufacturer's instructions. These arrays measured the concentrations for the Th1 and Th2 cytokines IFN-γ, IL-10, IL-13, IL-2, IL-4, IL-5, IL-6, IL-8, GM-CSF, and TNF-α, and for the checkpoint molecules B7-1 (CD80), B7-2 (CD86), B7-H1 (PD-L1), B7-H2 (ICOS L), B7-H3 (CD276), CD28 (Tp44), CTLA-4 (CD152), ICOS (CD278), PD-1 (CD279) and PD-L2 (B7-DC). All plasma exosome samples were normalized to a concentration of 50 µg. Plasma exosomes (100 µl per sample) were loaded on the arrays and incubated at 4° overnight. Data extraction was performed by RayBiotech.

Western Blot

Plasma exosomes from normal donors and glioma patients were lysed in buffer containing 50 mmol/l of NaCl, 50 mmol/l of NaF, 50 mmol/l of sodium pyrophosphate, 5 mmol/l of EDTA, 5 mmol/l of EGTA, 2 mmol/l of Na3VO4, 1% Triton X-100, 0.5 mmol/l of PMSF, 10 mmol/l of HEPES and 10 µg/ml leupeptin at pH 7.4. Soluble protein extracts (20 µg per sample) were loaded into polyacrylamide gels (12.5%, BIO-RAD No. 3450015) and transferred onto PVDF membranes (BIO-RAD No. 162-0175). Membranes were then incubated for 1 hour in blocking buffer followed by overnight incubation with primary antibodies to PD-L1 (Cell Signaling No. 136845), CD63 (Novus No. NB100-77913) and Flotillin-1 (Cell Signaling No. 3253S). The following day, after a 1-hour incubation with anti-rabbit (Jackson ImmunoResearch Laboratories No. 111-035-003) and anti-mouse (Jackson ImmunoResearch Laboratories No. 115-035-003) secondary antibodies, membranes were visualized by enhanced chemiluminescence.

IFN-γ ELISA

IFN-γ (R&D Systems No. DIF50) ELISA was performed accordingly to the protocol provided by the manufacturer. Plasma exosome samples from normal donors and GBM patients were measured in duplicate and each sample was normalized to a concentration of 50 µg.

Statistical Analysis

Statistical analysis was performed with GraphPad Prism software, using the two-tailed Student T-test. Statistical significance was determined at *P<0.05.

Results

One-Step DGU Isolates Exosomes from Normal Donors and Glioma Patients' Plasma

Figure 2A:
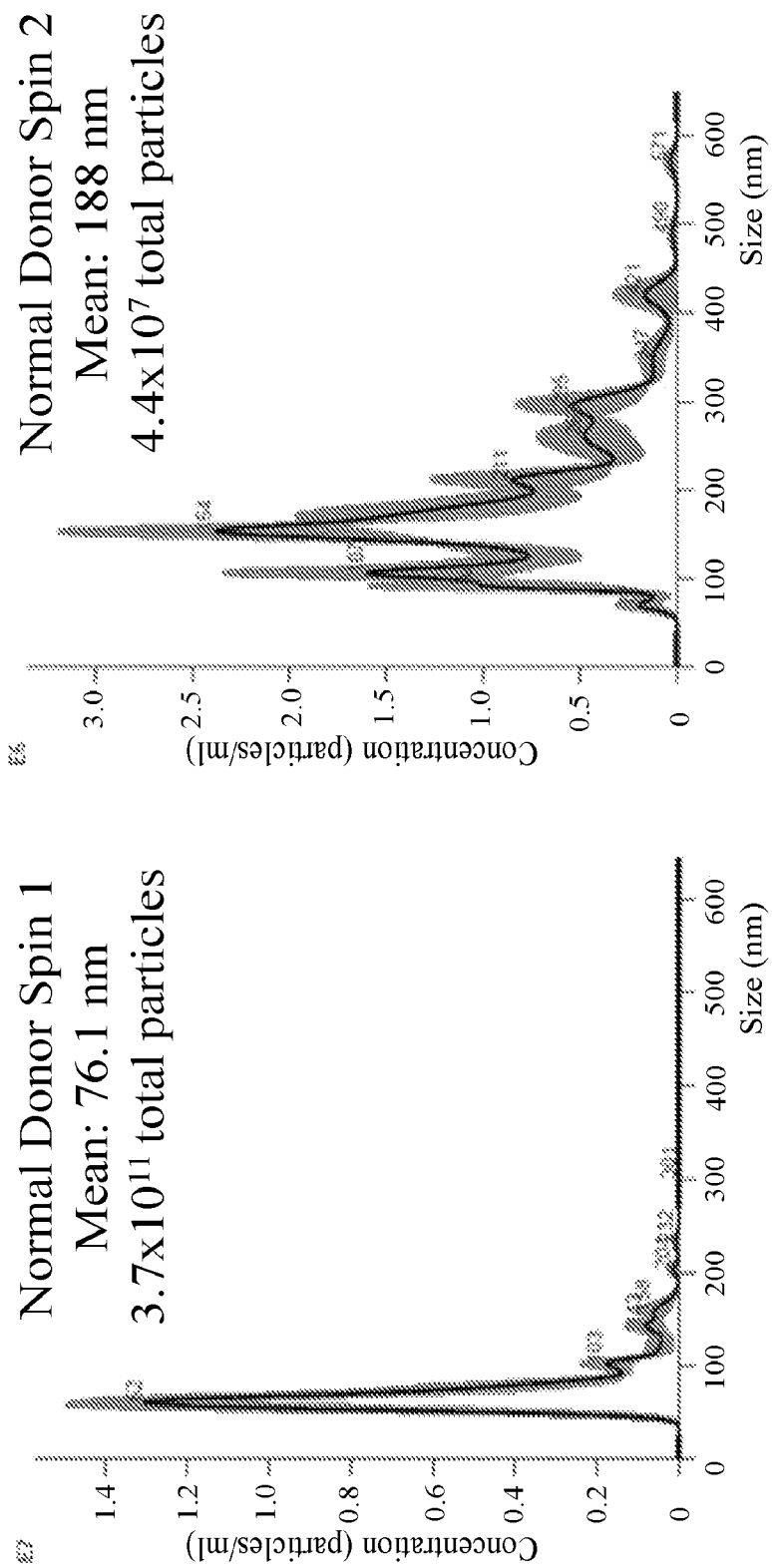
FIGS. 2A-2F show the impact of serial DGU on plasma exosome size and frequency. Representative nanoparticle tracker analysis histograms (A, D), photomicrographs (B, E), and pooled data for size and frequency (C, F; mean±SEM, n=20 per group, ***P<0.001) of plasma extracellular vesicles after one density gradient ultracentrifugation (Spin 1) and two serial density gradient ultracentrifugations (Spin 2) for normal donors (A-C) and glioblastoma patients (D-F). Note that for both normal donors and glioblastoma patients, extracellular vesicles isolated after a single ultracentrifugation (Spin 1) appear to be mostly <100 nm in diameter (i.e. exosomes). Performing two-step serial density gradient ultracentrifugation (Spin 2) results in particles that are both larger and less frequent. While this second spin is necessary to concentrate the samples for further molecular analysis, it appears to skew nanoparticle tracking results by causing aggregation of particles.
Figure 2B:
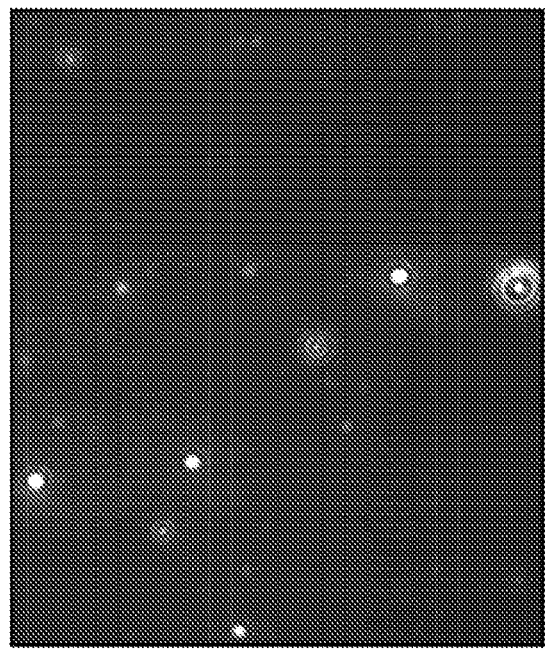
Figure 2B:
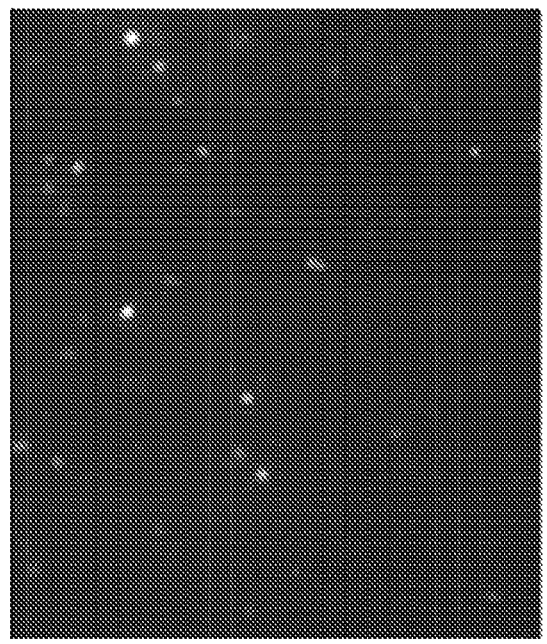
Figure 2C:
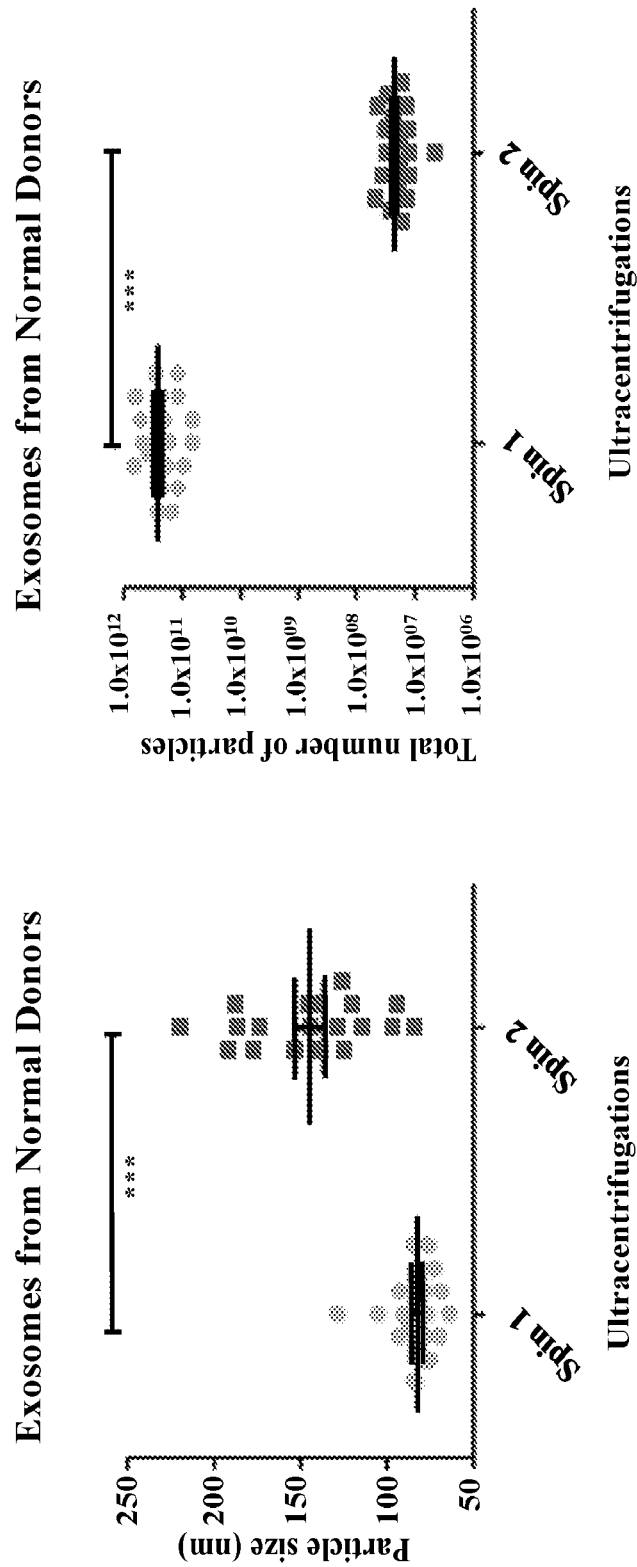
Figure 2D:
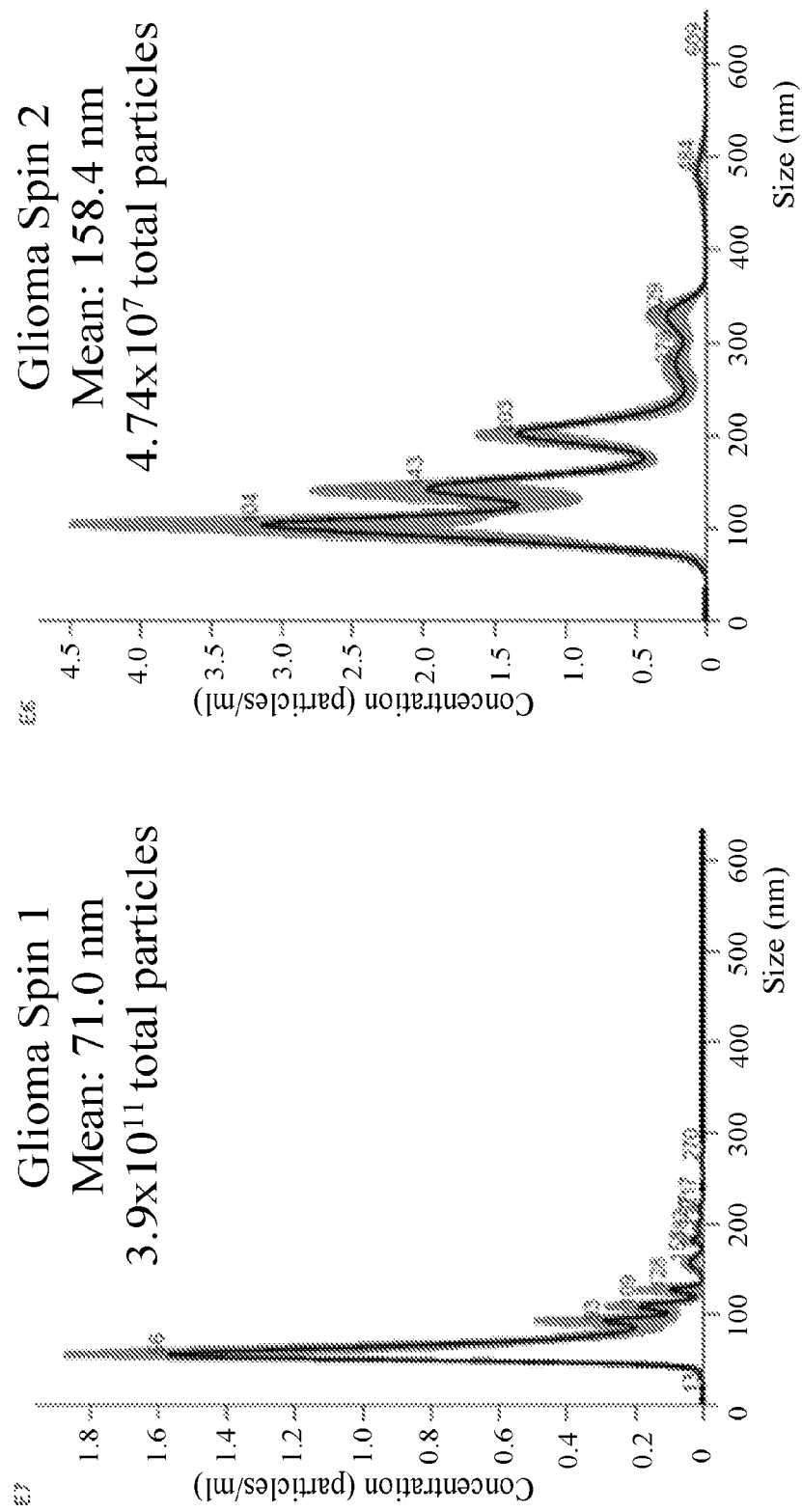
Figure 2E:
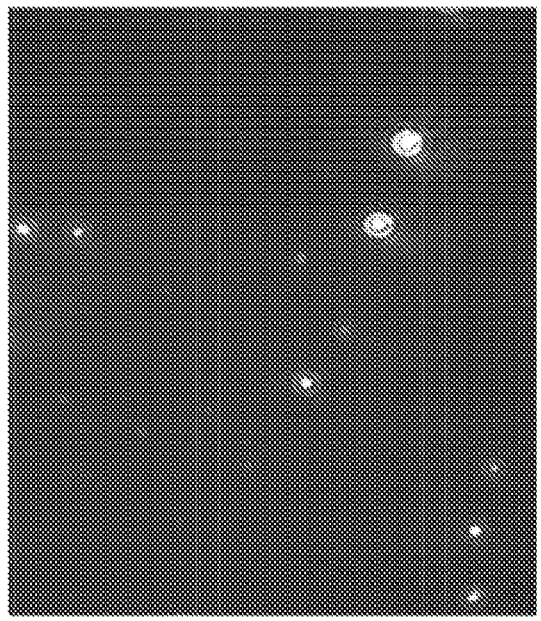
Figure 2E:
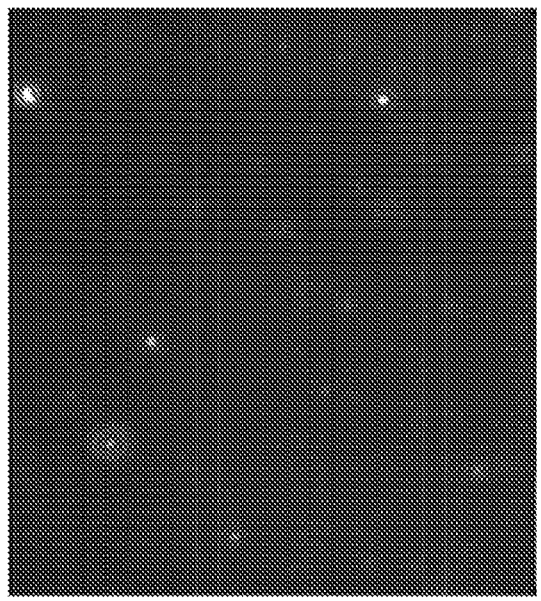
Figure 2F:
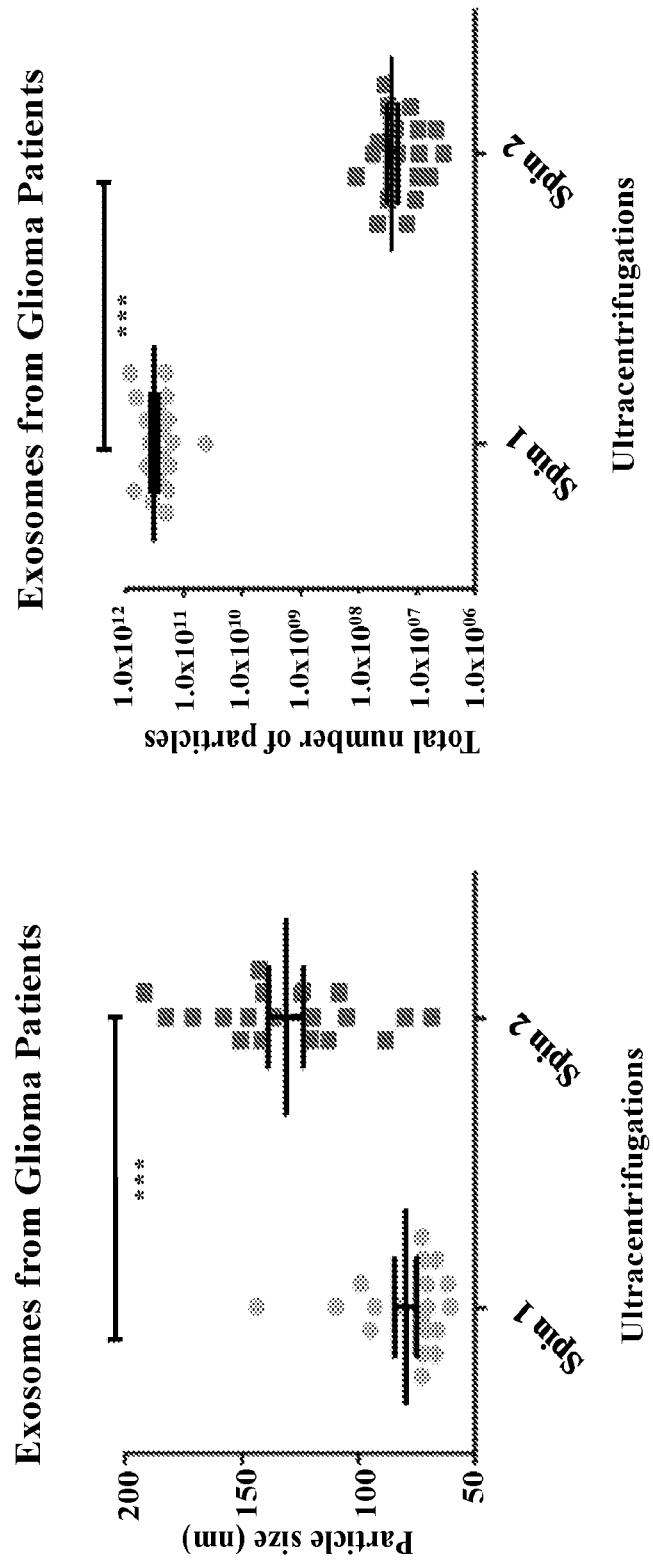

Exosomes isolated by our two-step DGU protocol were analyzed by nanotracker particle analysis to determine the size and concentration using light scattering and Brownian motion. One-step DGU (90 minutes) isolates a pure population of plasma exosomes quickly for nanotracker analysis. In contrast, the two-step DGU method takes an additional 16 hours (90 minutes+16 hours) to concentrate plasma exosomes efficiently for further analysis of their contents but results in exosome aggregation that skews nanotracker results (FIGS. 2A and D). Exosomes isolated by one-step DGU are physically smaller but more abundant than exosomes isolated by two-step DGU for both normal donors (FIGS. 2B and C) and glioma patients (FIGS. 2E and F).

Figure 3A:
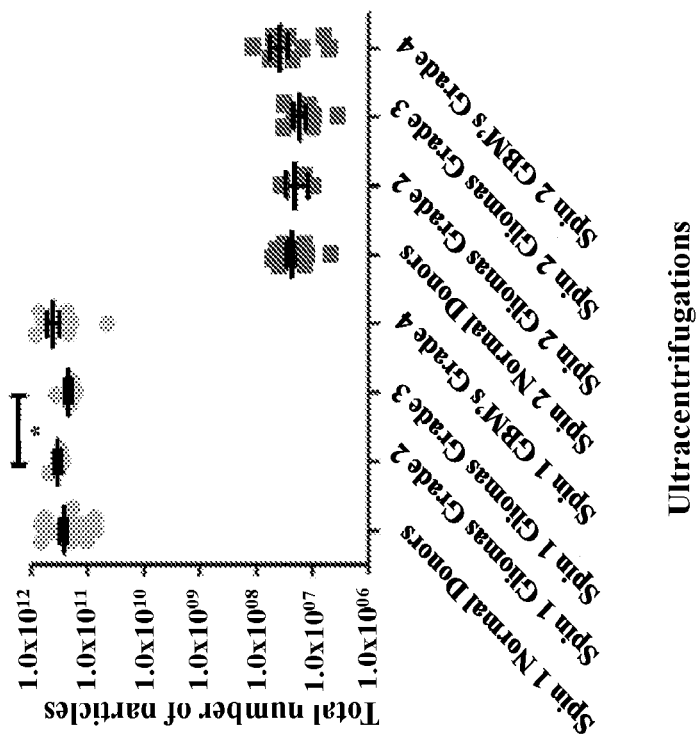
FIGS. 3A-3G shows that glioma patient exosomes are grossly similar to normal donors. Pooled nanoparticle tracking analysis results comparing size (A, C, E) and frequency (B, D, F) following Spin 1 and Spin 2 in normal donor to different glioma grades (A, B), newly diagnosed or recurrent gliomas (C, D) and IDH wild-type or IDH mutant gliomas (E, F). *P<0.05. Note that these results confirm increased size and decreased frequency of particles after Spin 2 compared to Spin 1 but show only mild differences between normal donors and glioma samples. (G) Western Blot analysis shows the exosomal markers Flotillin-1 and CD63 are found universally in plasma exosomes from normal donors, glioblastoma (grade 4) patients, and grade 3 glioma patients, though CD63 expression may be slightly reduced in glioma patients. Interestingly, the immunosuppressive checkpoint and T cell costimulatory homolog protein PD-L1 is found at similar levels in both normal donor and glioma patient plasma exosomes.
Figure 3B:
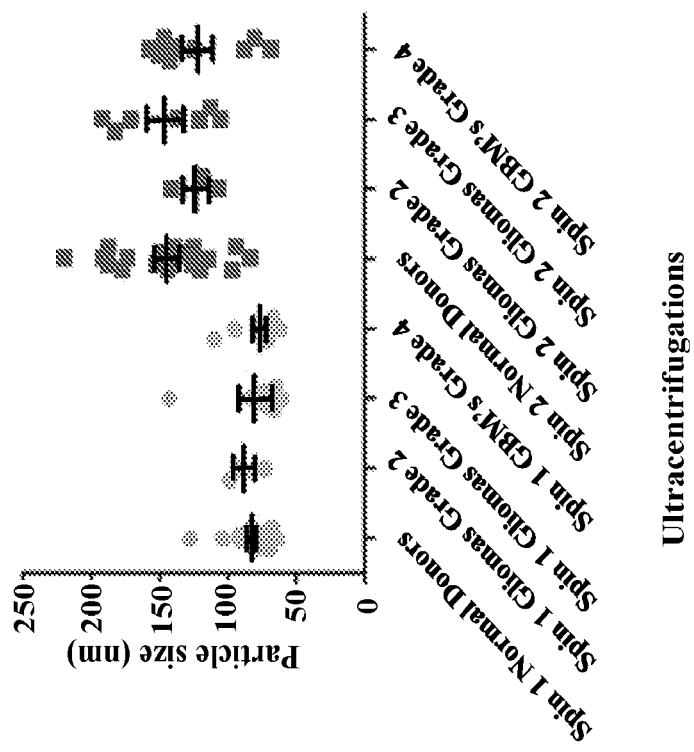
Figures 3C, 3D:
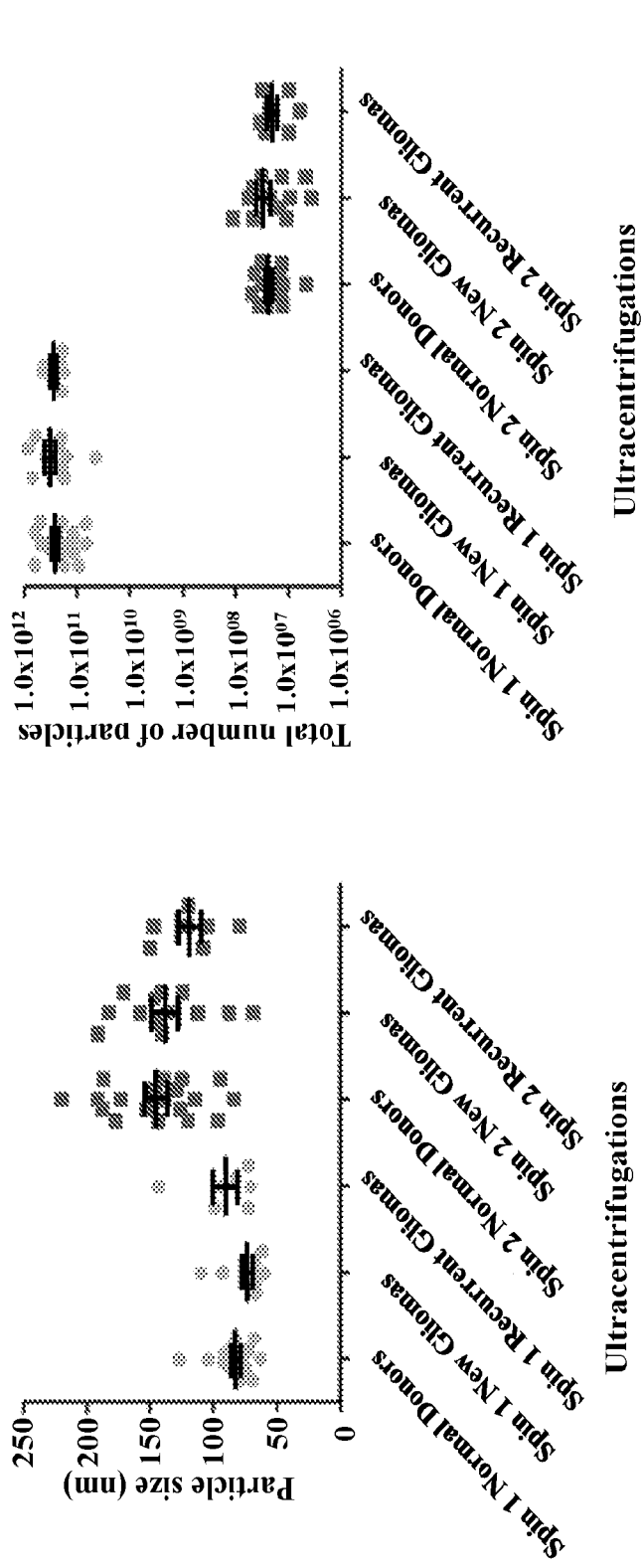
Figure 3E:
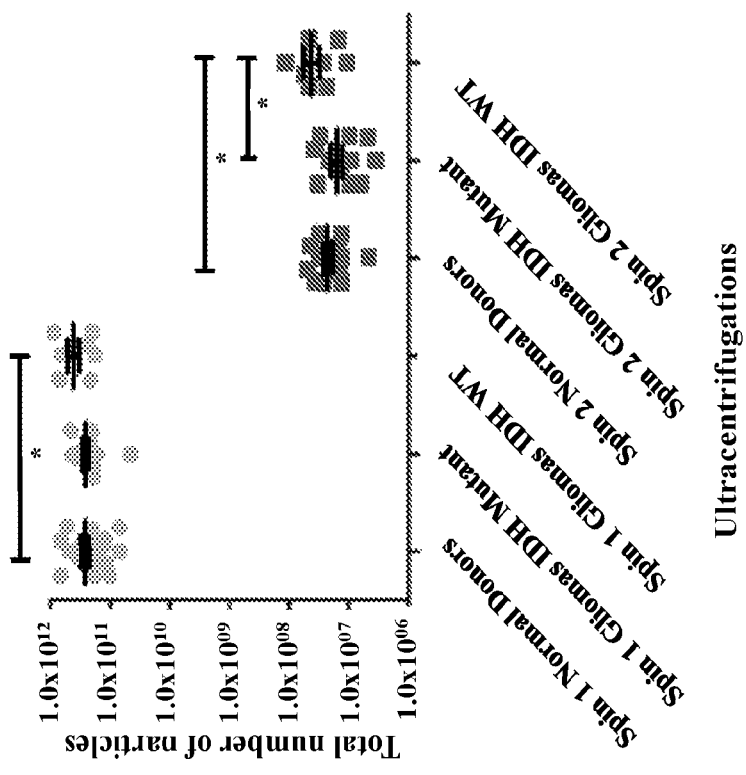
Figure 3F:
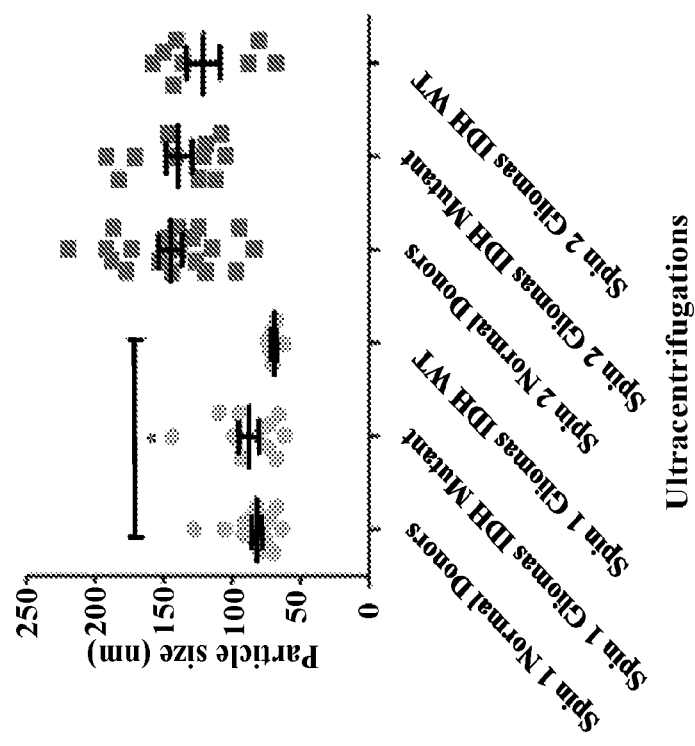

IDH Wild-Type Glioma Patients' Plasma Exosomes are Physically Smaller but Higher Concentration than Normal Donors Following two-step DGU, nanotracker analysis to determine size and concentration was also performed on exosomes isolated from glioma tumors that were grade 2, 3 or GBM grade 4 (FIGS. 3A and B), new or recurrent (FIGS. 3C and D) and IDH WT or mutant (FIGS. 3E and F). No significant differences in size and concentration were observed between one or two-step DGU for grade 2, 3 or 4, or between new or recurrent tumor patient plasma exosomes (FIGS. 3A, B, C, and D). However, following one-step DGU we identified significant differences between IDH WT and normal donors plasma' exosomes, with IDH WT exosomes physically smaller, but more abundant than normal donor plasma exosomes (FIGS. 3E and F). Following two-step DGU, significant differences were observed between normal donors and IDH WT exosomes and between IDH WT and mutant exosomes for particle concentration only.

Figure 3G:
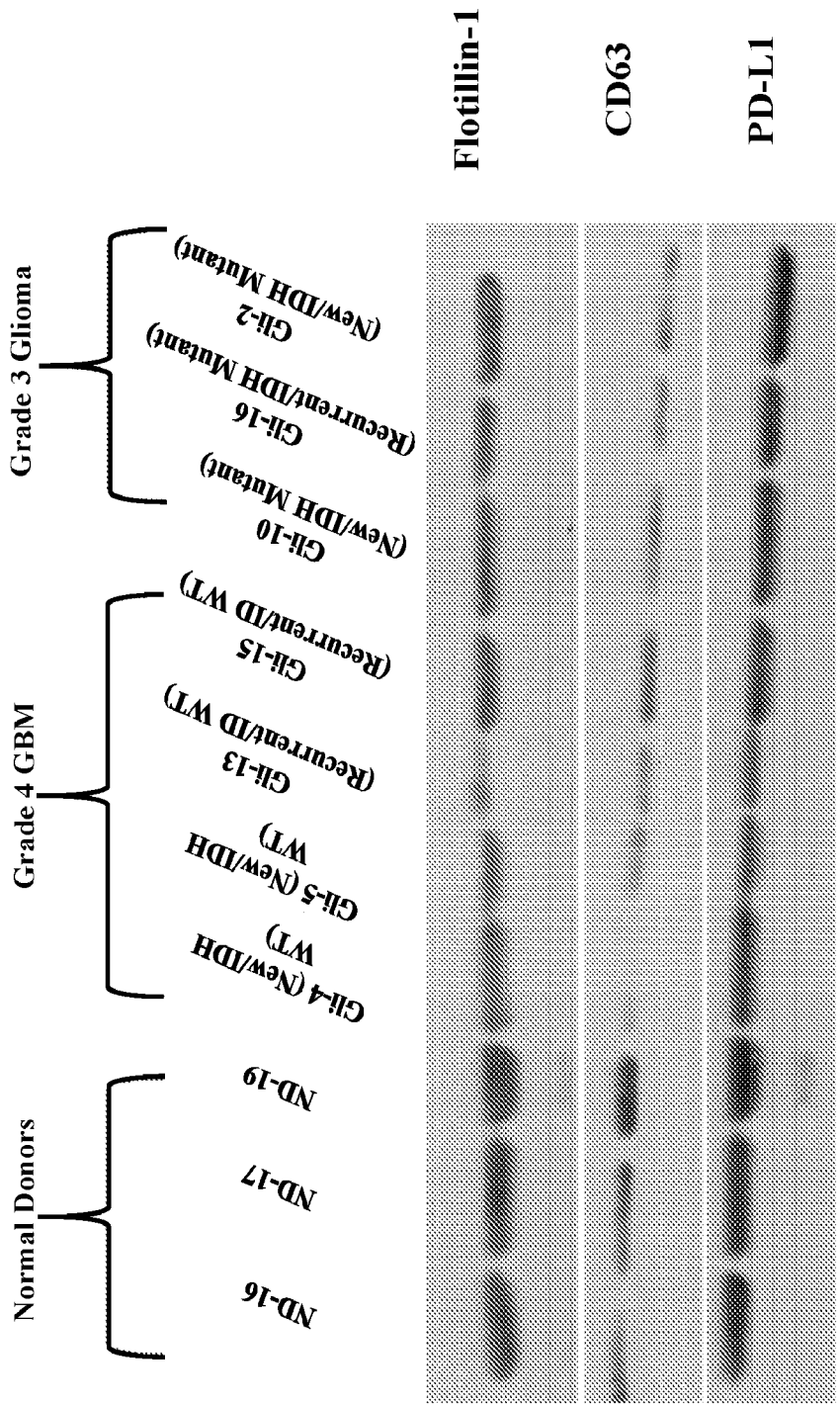

The Exosome Markers CD63 and Flotillin-1 and the Immunosuppressive Molecule Programmed Death-Ligand 1 (PD-L1) are Present in Both Glioma Patients' and Normal Donors' Plasma Exosomes Western blots were employed to evaluate the expression of the exosome markers CD63 and Flotillin-1 in glioma patients' and normal donors' plasma exosomes isolated by two-step DGU. Both CD63 and Flotillin-1 were detected in normal donors, grade 4 GBM and grade 3 glioma patients' exosomes, indicating again that our DGU protocol allows the isolation of exosomes (FIG. 3G). Interestingly, the immune checkpoint molecule PD-L1 was detected in all the exosome samples, including those from normal donors.

Figure 4A:
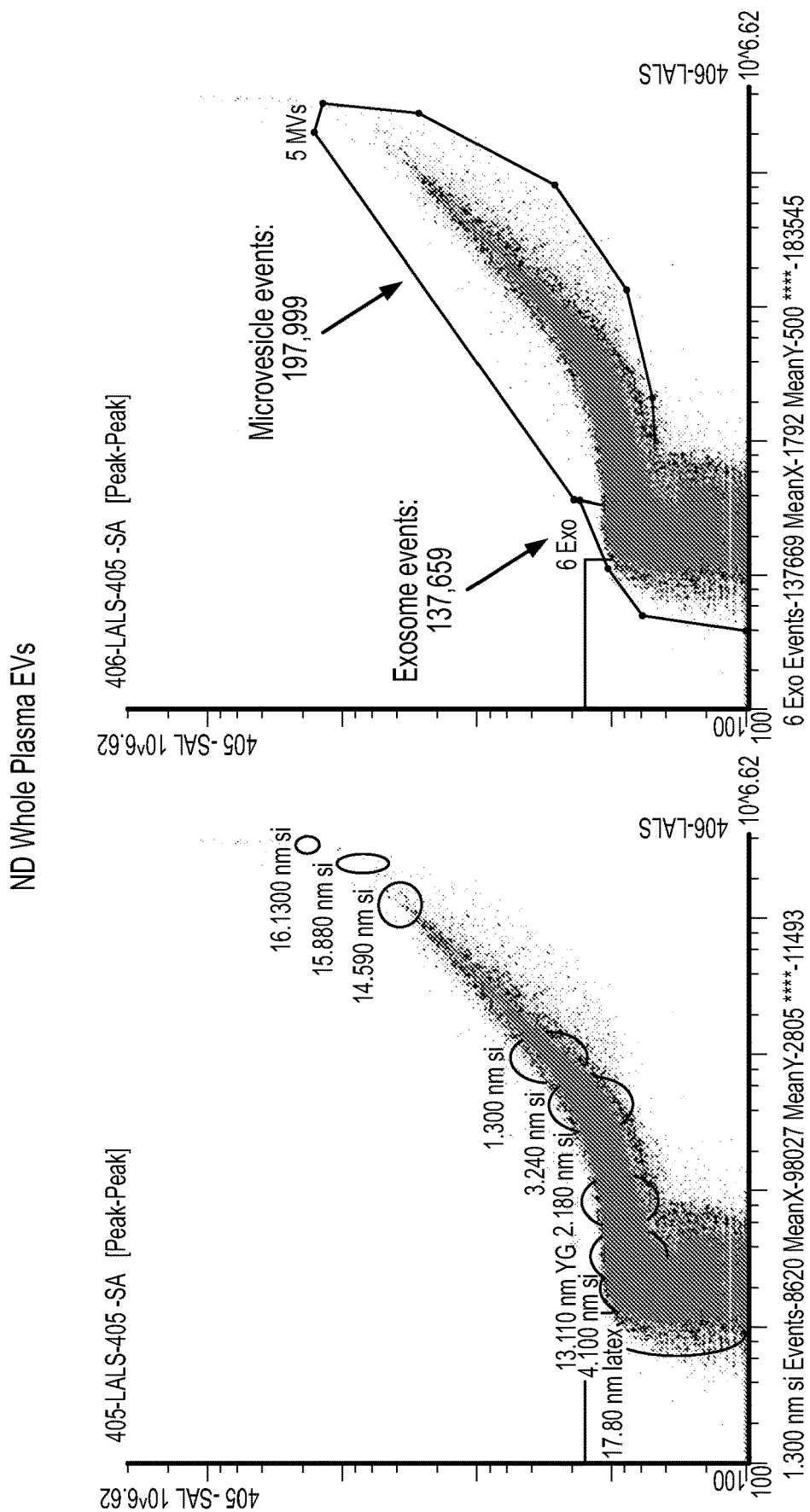
FIGS. 4A-4F shows that nanoscale flow cytometry confirms plasma exosome purification by serial DGU. An enriched exosomes population identified in whole plasma particles and exosomes isolated by one-step DGU and analyzed with nanoscale flow cytometry. Nanoscale flow cytometry representation of one normal donor (A) and one GBM (C) whole plasma EVs, illustrating exosome and microvesicle events. Nanoscale flow cytometry representation of one normal donor (B) and one GBM (D) isolated EVs using our one-step DGU protocol. An enriched population of exosomes and a decreased in the microvesicle population was observed. (E) Quantification of exosomes and microvesicles from whole plasma EVs-vs-density gradient isolated EVs, confirming enrichment of exosomes and decreased in microvesicles using the DGU protocol described herein. An increased in microvesicles was observed in GBM whole plasma EVs in comparison to ND whole plasma EVs. (F) Particle sizes of whole plasma and isolated EVs using our DGU method. An enriched population of particles that were <100 nm (exosomes) was observed employing our DGU method, whereas particles that were 100-1,000 nm (microvesicles) were reduced. In GBM whole plasma, particles that were 100-200 nm (microvesicles) were enriched in comparison to ND whole plasma (mean±SEM, n=3/group, *P <0.001, P<0.01).
Figure 4B:
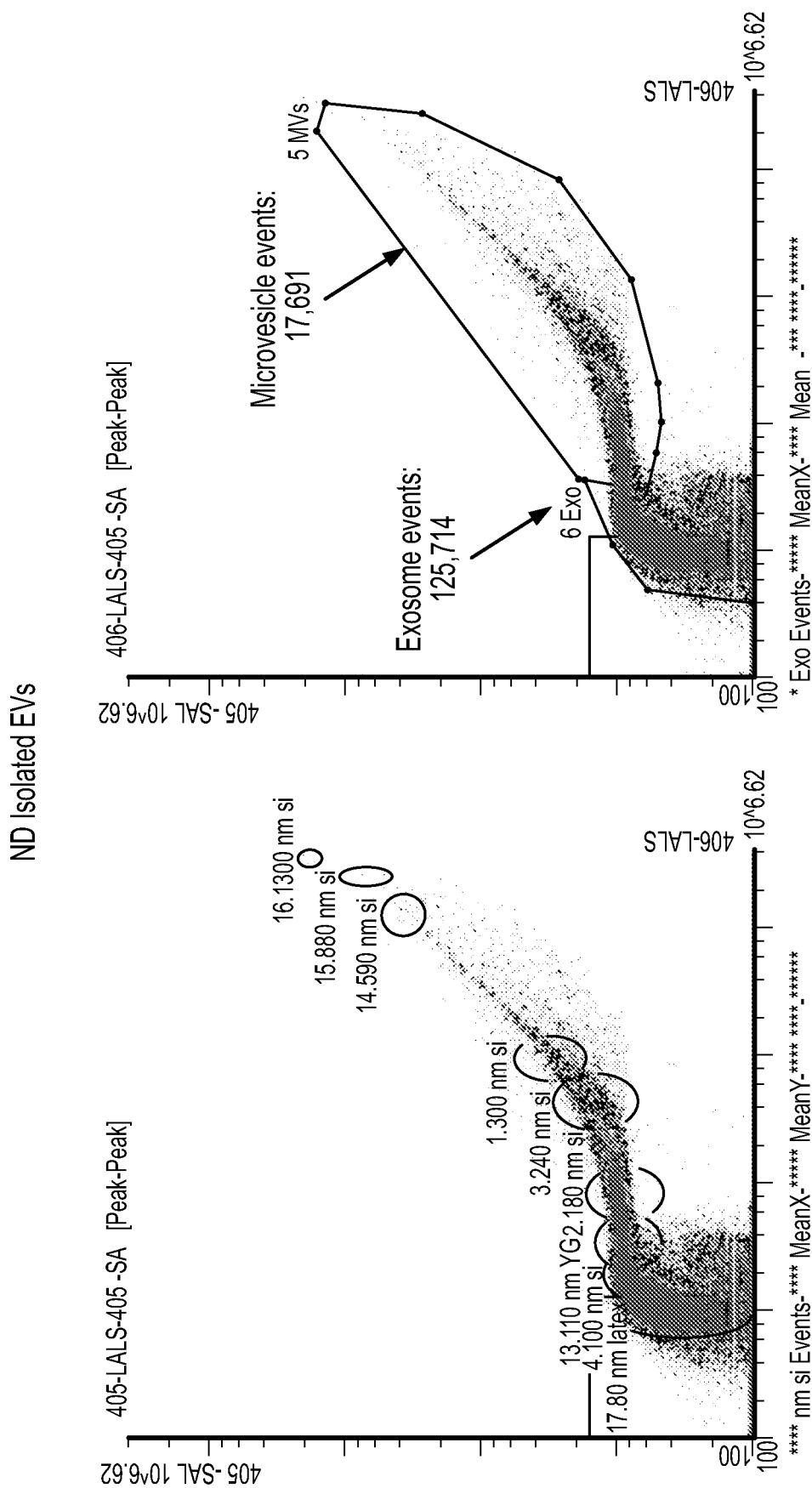
Figure 4C:
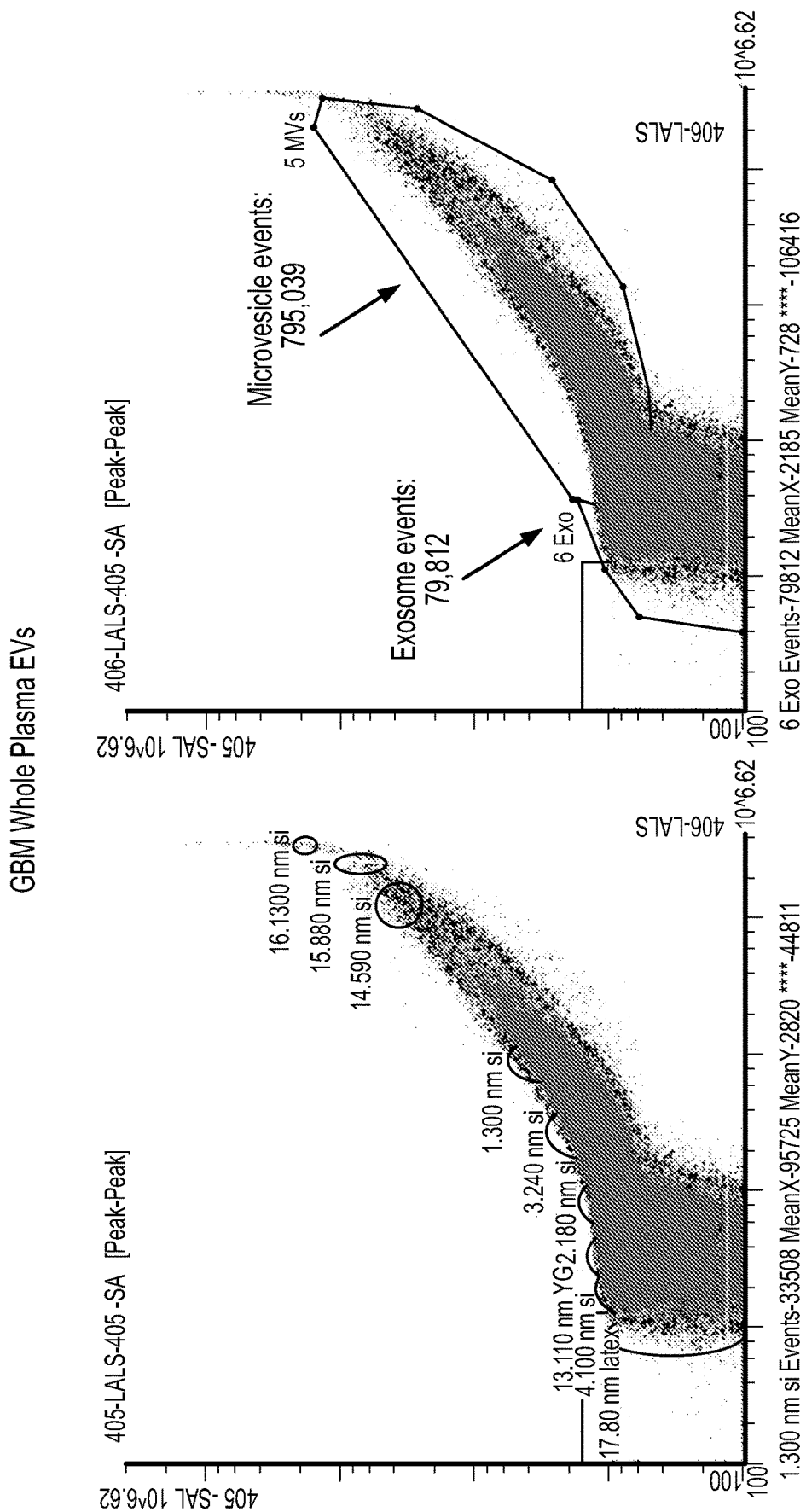
Figure 4D:
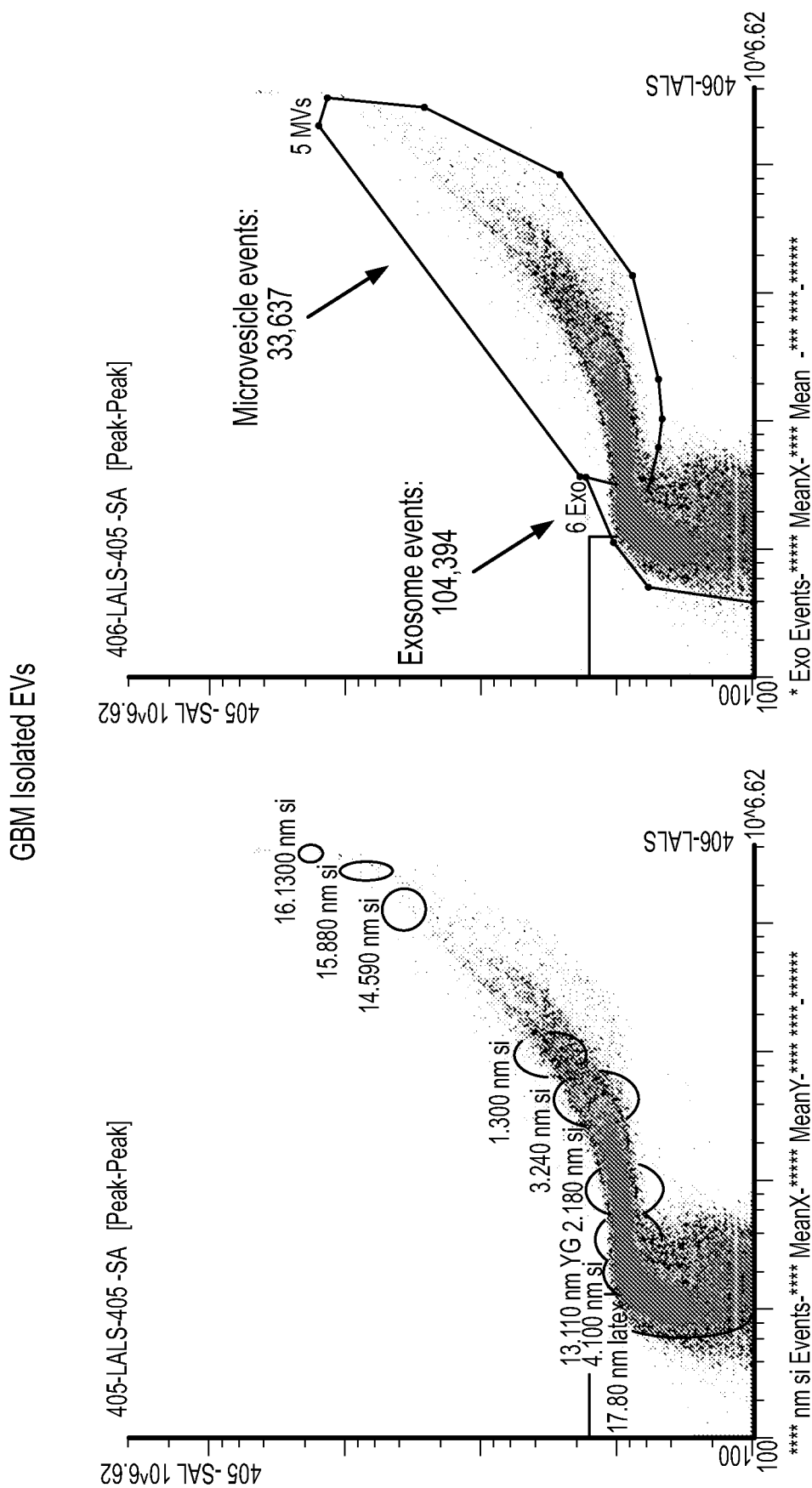
Figure 4E:
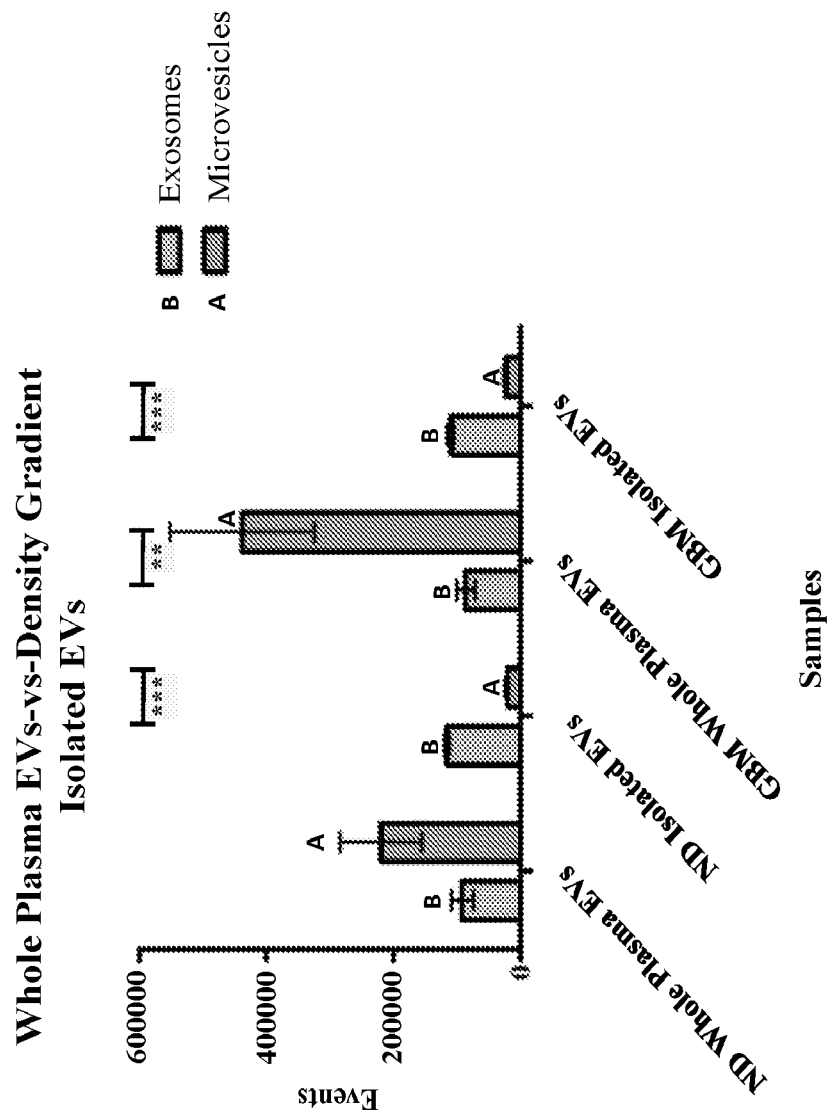
Figure 4F:
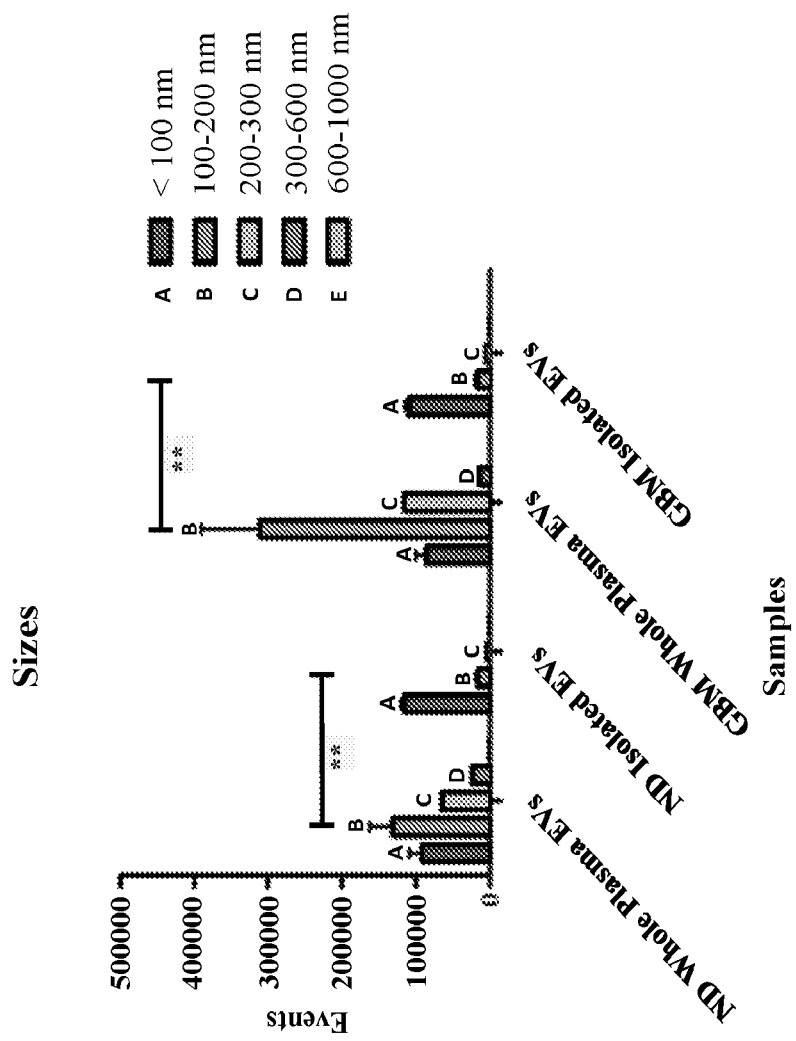

Nanoscale Flow Cytometry Analysis Detected a Pure Population of Plasma-Derived Exosomes Isolated by DGU Microparticles from GBM patients' and normal donors' whole plasma were compared to exosomes samples isolated employing our DGU one-step protocol. Nanoscale flow cytometry analysis showed an enriched pure population of exosomes in both normal donors (FIGS. 4A, B, and E) and GBM patients (FIGS. 4C, D, and E) after samples were processed using our DGU protocol. Interestingly, in the GBM whole plasma samples (FIG. 4 C), there was an increased in microvesicles in comparison to normal donors' whole plasma (FIGS. 4A and E). However, the number of microvesicles in both normal donors and GBM patients was reduced significantly in comparison to whole plasma samples after DGU was performed (FIG. 4 E). Particle size was assessed using calibration beads further demonstrating that our method enriched for exosomes (<100 nm) instead of microvesicles (100-1,000 nm), and that there is an increased in microvesicles (100-200 nm) in GBM whole plasma samples in comparison to normal donor whole plasma (FIG. 4F).

Figure 5B:
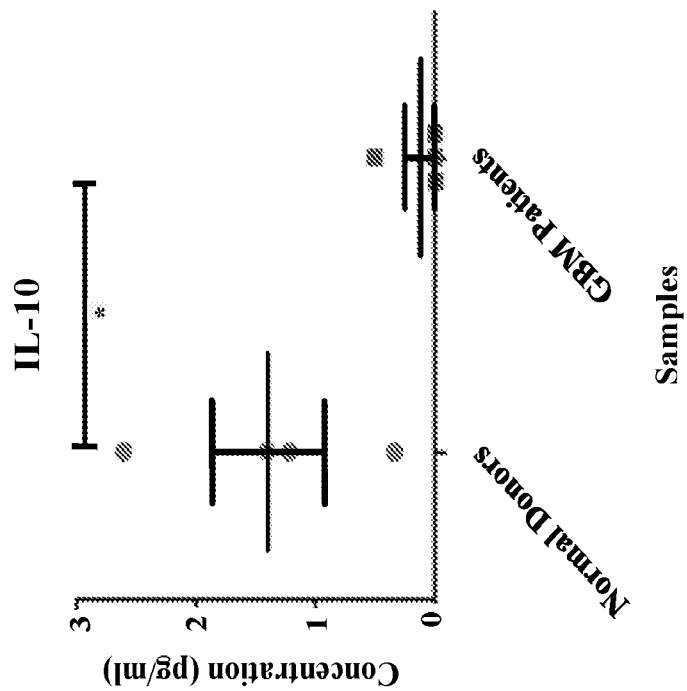
FIGS. 5A-5C are cytokine arrays from plasma exosomes showed a decreased concentration of IFN-γ, IL-10, and IL-13 in GBM patients in comparison to normal donors. Quantification of IFN-γ (A), IL-10 (B), and IL-13 (C) in plasma exosomes from normal donors and grade 4 GBM patients' plasma exosomes. (mean±SEM, n=4/group, *P<0.05).
Figure 5A:
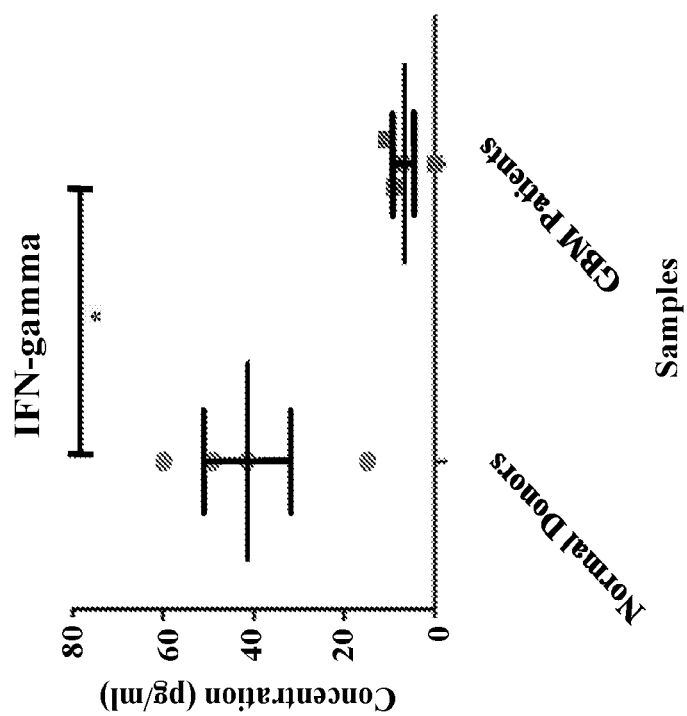
Figure 5C:
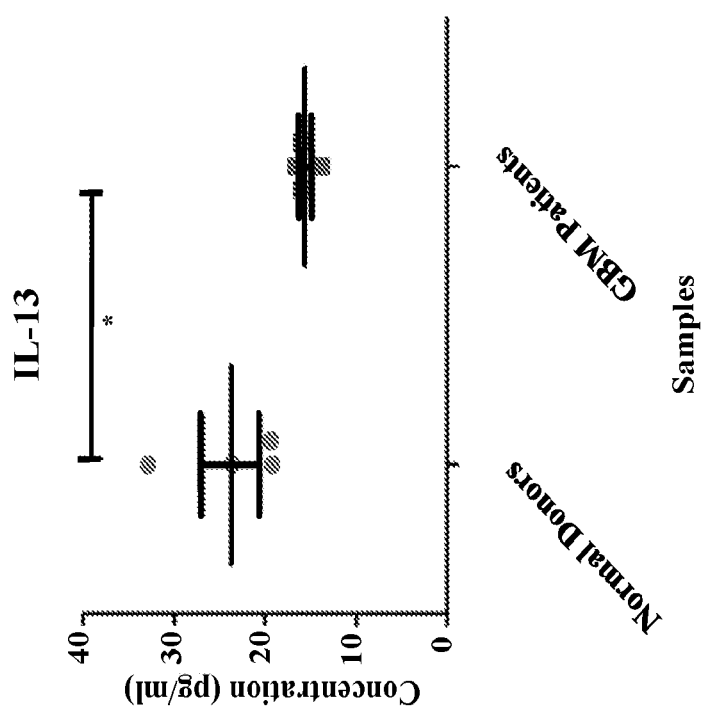
Figure 6:
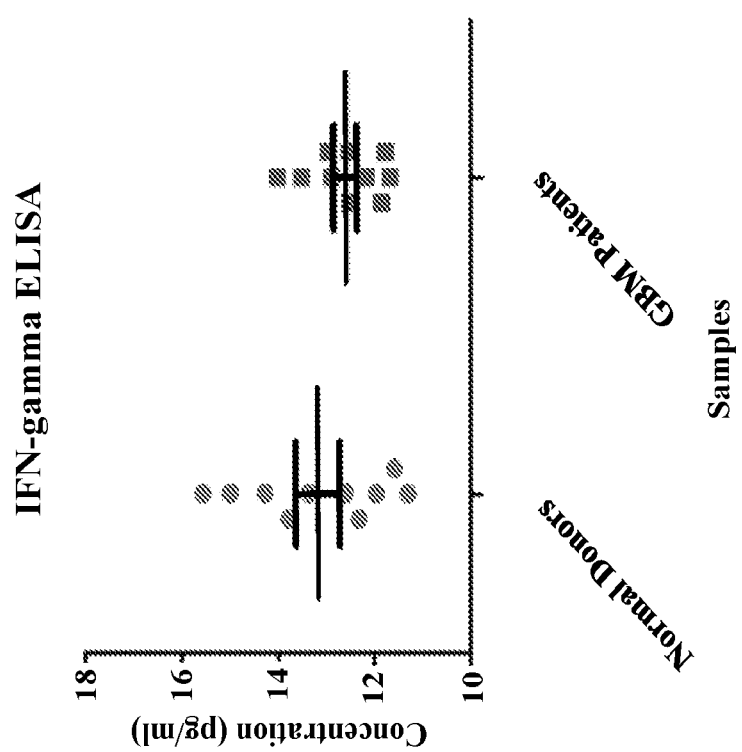
FIG. 6 shows an IFN-γ ELISA of plasma exosomes from normal donors and grade 4 GBM patients. Analysis of plasma exosomes from normal donors and GBM patients suggests a decreased concentration of IFN-γ in GBM patients' plasma exosomes in comparison to normal donors, although these differences were less pronounced in comparison to the cytokine microarray analysis.
Figure 7B:
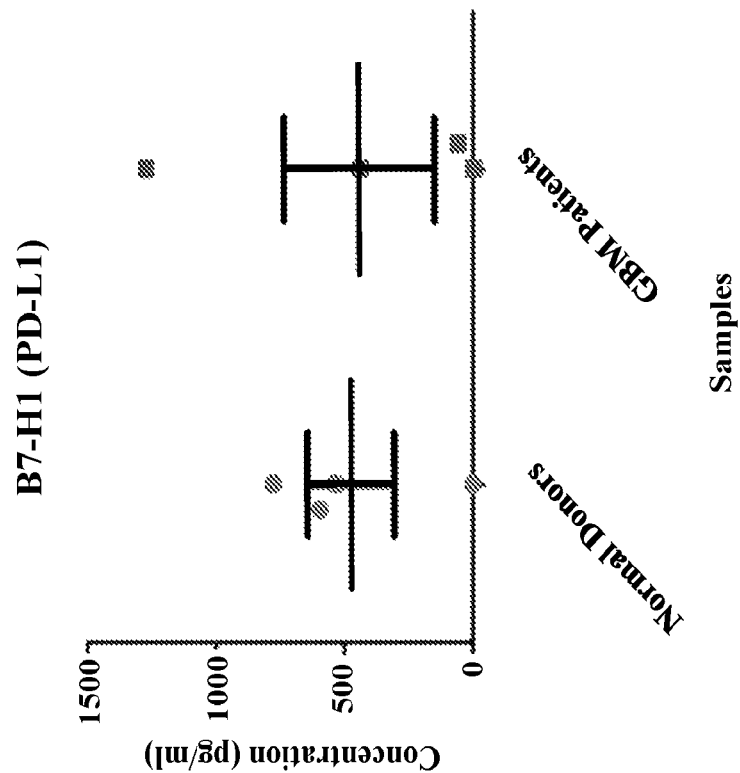
FIGS. 7A-7D contain checkpoint molecule arrays from plasma exosomes showing a decreased concentration of CD80, PD-L1, CD86, and ICOSL in GBM patients in comparison to normal donors. Quantification of CD80 (A), PD-L1 (B), CD86 (C), and ICOSL (D) in plasma exosomes from normal donors and grade 4 GBM patients' plasma exosomes (mean±SEM, n=4/group).
Figure 7A:
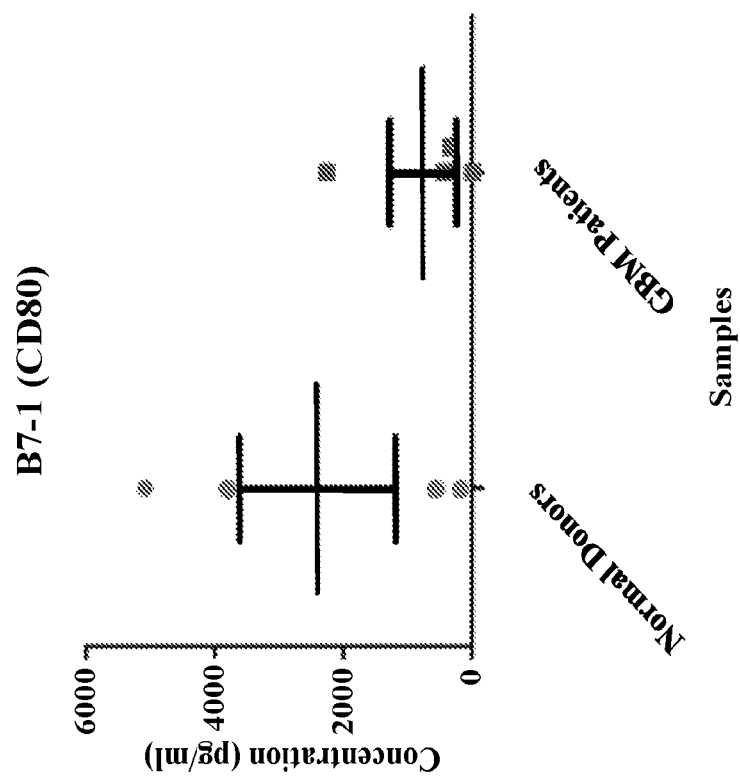
Figures 7C, 7D:
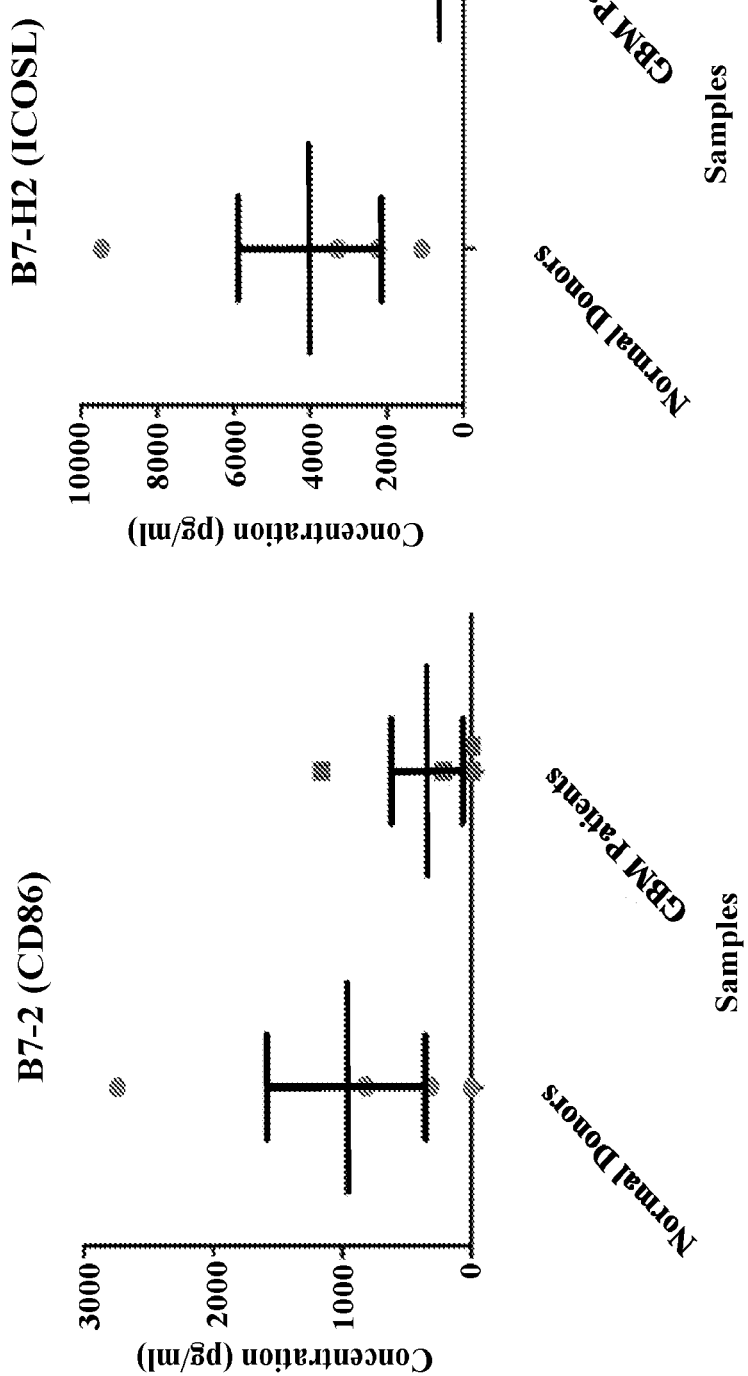

Cytokine Arrays Showed Decreased Concentration of IFN-γ, IL-10, and IL-13 Cytokines in GBM Patients' Plasma Exosomes Cytokine arrays were employed using plasma exosomes isolated from grade 4 GBM patients and normal donors. Expression of 10 cytokines was evaluated (Table 1). We found a significantly decreased concentration of the cytokines IFN-γ, IL-10, and IL-3 in GBM patients' plasma exosomes in comparison to normal donor exosomes (FIGS. 5A, B, and C). Similar IFN-γ results were seen with ELISA though the effect was less pronounced than by microarray analysis (FIG. 6).

TABLE 1

Cytokines Array

| Cytokines | Source | Concentration (pg/ml) | P value |
| --- | --- | --- | --- |
| IFN-γ | ND | 41.38 ± 19.13 | 0.013 |
|  | GBM | 6.880 ± 4.770 |  |
| IL-10 | ND | 1.396 ± 0.9394 | 0.040 |
|  | GBM | 0.1259 ± 0.2519 |  |
| IL-13 | ND | 23.84 ± 6.364 | 0.045 |
|  | GBM | 15.61 ± 1.291 |  |
| IL-2 | ND | 25.62 ± 5.247 | 0.266 |
|  | GBM | 22.32 ± 1.176 |  |
| IL-4 | ND | 0 | — |
|  | GBM | 0 |  |
| IL-5 | ND | 8.3394 ± 1.317 | 0.360 |
|  | GBM | 7.650 ± 0.4464 |  |
| IL-6 | ND | 0 | — |
|  | GBM | 0 |  |
| IL-8 | ND | 17.09 ± 8.236 | 0.059 |
|  | GBM | 6.958 ± 2.810 |  |
| GM-CSF | ND | 9.091 ± 6.420 | 0.300 |
|  | GBM | 4.882 ± 3.729 |  |
| TNF-α | ND | 16.53 ± 25.58 | — |
|  | GBM | 0 |  |

Checkpoint Molecule Arrays Showed Decreased Concentration of Pro-Inflammatory B7-1, B7-2, and ICOSL in GBM Patients' Exosomes Using plasma exosomes from grade 4 GBM patients and normal donors, checkpoint molecules arrays were used to measure the concentration of 10 costimulatory molecules necessary for T cell activation and survival from plasma exosomes (Table 2). Trends towards decreased expression were observed for CD80, CD86, and ICOSL between GBM patients and normal donors but these were not statistically significant (FIG. 7A-D). PD-L1 expression was the same between normal donors and GBM patients (FIG. 7B), confirming our western blot results for PD-L1 expression (FIG. 3G).

TABLE 2

Checkpoint Molecules Array

| Checkpoint Molecules | Source | Concentration (pg/ml) | P value |
| --- | --- | --- | --- |
| B7-1 (CD80) | ND | 2408 ± 2418 | 0.257 |
|  | GBM | 763.3 ± 1025 |  |
| B7-2 (CD86) | ND | 973.4 ± 1225 | 0.390 |
|  | GBM | 348.3 ± 555.6 |  |
| B7-H1 (PD-L1) | ND | 475.4 ± 334.2 | 0.931 |
|  | GBM | 444.7 ± 587.0 |  |
| B7-II2 (ICOSL) | ND | 4016 ± 3739 | 0.121 |
|  | GBM | 628.8 ± 256.2 |  |
| B7-H3 (CD276) | ND | 0 | — |
|  | GBM | 0 |  |
| CD28 (Tp44) | ND | 175.6 ± 129.8 | 0.274 |
|  | GBM | 65.03 ± 130.1 |  |
| CTLA-4 (CD152) | ND | 0 | — |
|  | GBM | 0 |  |
| ICOS (CD278) | ND | 1510 ± 184.1 | 0.691 |
|  | GBM | 1406 ± 464.5 |  |
| PD-1 (CD279) | ND | 62.83 ± 73.36 | 0.760 |
|  | GBM | 95.73 ± 191.5 |  |
| PD-L2 (B7-DC) | ND | 990.6 ± 187.5 | 0.572 |
|  | GBM | 1132 ± 435.1 |  |

These results demonstrate that serial DGU efficiently isolates plasma exosomes with distinct differences between GBM patients and normal donors, and that plasma exosomes can be used as a non-invasive biomarker for cancer.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a mammal having glioblastoma cancer, wherein said method comprises:
   (a) identifying extracellular vesicles (EVs) in a sample from said mammal, wherein said EVs have reduced levels of one or more immunomodulatory polypeptides as compared to a sample obtained from a mammal not having said cancer, wherein said one or more immunomodulatory polypeptides is selected from IFN-γ, IL-10, IL-13, CD80, CD86, and ICOSL; and
   (b) administering a cancer treatment to said mammal having cancer, wherein said cancer treatment is selected from the group consisting of surgery, radiation therapy, chemotherapy, tumor treating fields (TTF) therapy, targeted therapy, hormone therapy, angiogenesis inhibitor therapy, tumor vaccination, checkpoint blockade therapy, and any combinations thereof.

2. The method of claim 1, wherein said mammal is a human.

3. The method of claim 1, wherein said sample is a blood sample.

4. The method of claim 1, wherein said EVs are exosomes.

5. The method of claim 4, wherein the longest diameter of said exosomes is less than about 100 nm.

6. A method for treating glioblastoma cancer, wherein said method comprises administering a cancer treatment to a mammal having cancer and identified as having extracellular vesicles (EVs) having a reduced level of one or more immunomodulatory polypeptides as compared to the level of said one or more immunomodulatory polypeptides present in EVs obtained from a control mammal not having said cancer, wherein said one or more immunomodulatory polypeptides is selected from IFN-γ, IL-10, IL-13, CD80, CD86, and ICOSL, and wherein said cancer treatment is selected from the group consisting of surgery, radiation therapy, chemotherapy, tumor treating fields (TTF) therapy, targeted therapy, hormone therapy, angiogenesis inhibitor therapy, tumor vaccination, checkpoint blockade therapy, and any combinations thereof.

7. The method of claim 6, wherein said mammal is a human.

8. The method of claim 6, wherein said EVs are exosomes.

9. The method of claim 8, wherein the longest diameter of said exosomes is less than about 100 nm.

* * * * *

UNITED STATES PATENT AND TRADEMARK OFFICE
CERTIFICATE OF CORRECTION

| | | |
|---|---|---|
| PATENT NO. | : 12,000,834 B2 | Page 1 of 1 |
| APPLICATION NO. | : 16/762976 | |
| DATED | : June 4, 2024 | |
| INVENTOR(S) | : Cumba-Garcia et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 722 days.

Signed and Sealed this
Eighth Day of October, 2024

Katherine Kelly Vidal
*Director of the United States Patent and Trademark Office*